(12) United States Patent
Weitzner et al.

(10) Patent No.: US 8,187,229 B2
(45) Date of Patent: May 29, 2012

(54) COAXIAL CATHETER SYSTEM

(75) Inventors: Barry Weitzner, Acton, MA (US); Gary S. Rogers, Wenham, MA (US); Albert Solbjor, Waltham, MA (US)

(73) Assignee: Hansen Medical, Inc., Mountain View, CA (US)

( * ) Notice: Subject to any disclaimer, the term of this patent is extended or adjusted under 35 U.S.C. 154(b) by 621 days.

(21) Appl. No.: 11/762,749

(22) Filed: Jun. 13, 2007

(65) Prior Publication Data

US 2007/0239106 A1    Oct. 11, 2007

Related U.S. Application Data

(63) Continuation of application No. 11/467,886, filed on Aug. 28, 2006, which is a continuation of application No. 10/270,740, filed on Oct. 11, 2002, now abandoned, and a continuation-in-part of application No. 10/216,069, filed on Aug. 8, 2002, now abandoned, and a continuation-in-part of application No. 10/023,024, filed on Nov. 16, 2001, now abandoned, and a continuation-in-part of application No. 10/011,371, filed on Nov. 16, 2001, now Pat. No. 7,090,683, and a continuation-in-part of application No. 10/011,449, filed on Nov. 16, 2001, now abandoned, and a continuation-in-part of application No. 10/010,150, filed on Nov. 16, 2001, now Pat. No. 7,214,230, and a continuation-in-part of application No. 10/022,038, filed on Nov. 16, 2001, now abandoned, and a continuation-in-part of application No. 10/012,586, filed on Nov. 16, 2001, now Pat. No. 7,371,210.

(60) Provisional application No. 60/332,287, filed on Nov. 21, 2001, provisional application No. 60/313,495, filed on Aug. 21, 2001, provisional application No. 60/269,200, filed on Feb. 15, 2001, provisional application No. 60/276,217, filed on Mar. 15, 2001, provisional application No. 60/276,086, filed on Mar. 15, 2001, provisional application No. 60/276,152, filed on Mar. 15, 2001, provisional application No. 60/293,346, filed on May 24, 2001.

(51) Int. Cl.
*A61M 5/178* (2006.01)

(52) U.S. Cl. ... 604/158; 128/898; 604/108; 604/164.01; 604/171; 604/159; 604/65; 604/95.01; 604/103.1; 604/529; 606/79

(58) Field of Classification Search ............. 128/898; 604/50, 65, 95.01, 103.1, 108, 158, 159, 604/164.01, 171, 529; 606/79
See application file for complete search history.

(56) References Cited

U.S. PATENT DOCUMENTS 3,414,137 A    12/1968  Fortin
(Continued)

FOREIGN PATENT DOCUMENTS

EP    0683016 A1    5/1995
(Continued)

OTHER PUBLICATIONS

Ikuta et al., "Shape Memory Alloy Servo Actuator System with Electric Resistance Feedback and Application for Active Endoscope", 1988 IEEE, CH2555-1/88/0000/0427-430.

(Continued)

*Primary Examiner* — Nicholas Lucchesi
*Assistant Examiner* — Scott Medway
(74) *Attorney, Agent, or Firm* — Vista IP Law Group LLP

(57) ABSTRACT

A medical system comprises a first medical probe having indicia, and a second medical probe in a coaxial arrangement with the first medical probe. The second medical probe has a detector (e.g., an optical detector) configured for detecting a passage of the indicia as the first and second medical probes are moved relative to each other. In one embodiment, the first medical probe is an inner medical probe, and the second medical probe is an outer medical probe. The medical system further comprises an electromechanical driver coupled to the first and second medical probes, and a controller configured for directing the electromechanical driver to move the first and second medical probes relative to each other, and for receiving signals from the detector indicating the relative movement between the first and second medical probes.

20 Claims, 24 Drawing Sheets

U.S. PATENT DOCUMENTS

| | | | |
|---|---|---|---|
| 4,148,307 A | 4/1979 | Utsugi | |
| 4,402,310 A | 9/1983 | Kimura | |
| 4,512,348 A | 4/1985 | Uchigaki et al. | |
| 4,604,016 A | 8/1986 | Joyce | |
| 4,650,467 A | 3/1987 | Bonello et al. | |
| 4,654,024 A | 3/1987 | Crittenden et al. | |
| 4,655,746 A * | 4/1987 | Daniels et al. | 604/509 |
| 4,702,250 A | 10/1987 | Ovil et al. | |
| 4,750,475 A | 6/1988 | Yoshihashi | |
| 4,853,874 A | 8/1989 | Iwamoto et al. | |
| 4,911,163 A | 3/1990 | Fina | |
| 4,921,478 A | 5/1990 | Solano et al. | |
| 4,930,494 A | 6/1990 | Takehana et al. | |
| 4,941,454 A | 7/1990 | Wood et al. | |
| 4,960,411 A * | 10/1990 | Buchbinder | 604/95.01 |
| 4,977,886 A | 12/1990 | Takehana et al. | |
| 4,979,949 A | 12/1990 | Matsen, III et al. | |
| 5,030,201 A | 7/1991 | Palestrant | |
| 5,052,402 A | 10/1991 | Bencini et al. | |
| 5,072,361 A | 12/1991 | Davis et al. | |
| 5,078,140 A | 1/1992 | Kwoh | |
| 5,084,054 A | 1/1992 | Bencini et al. | |
| 5,086,401 A | 2/1992 | Fung et al. | |
| 5,116,180 A | 5/1992 | Fung et al. | |
| 5,154,717 A | 10/1992 | Matsen, III et al. | |
| 5,172,700 A | 12/1992 | Bencini et al. | |
| 5,174,278 A | 12/1992 | Babkow | |
| 5,184,601 A | 2/1993 | Putman | |
| 5,217,003 A | 6/1993 | Wilk | |
| 5,236,432 A | 8/1993 | Matsen, III et al. | |
| 5,238,002 A | 8/1993 | Devlin et al. | |
| 5,238,005 A | 8/1993 | Imran | |
| 5,246,421 A * | 9/1993 | Saab | 606/194 |
| 5,271,381 A | 12/1993 | Ailinger et al. | |
| 5,287,861 A | 2/1994 | Wilk | |
| 5,295,958 A | 3/1994 | Shturman | |
| 5,299,288 A | 3/1994 | Glassman et al. | |
| 5,312,361 A | 5/1994 | Zadini et al. | |
| 5,337,732 A | 8/1994 | Grundfest et al. | |
| 5,339,799 A | 8/1994 | Kami et al. | |
| 5,342,306 A | 8/1994 | Don Michael | |
| 5,347,987 A | 9/1994 | Feldstein et al. | |
| 5,350,355 A | 9/1994 | Sklar | |
| 5,356,375 A | 10/1994 | Higley | |
| 5,368,015 A | 11/1994 | Wilk | |
| 5,372,147 A | 12/1994 | Lathrop, Jr. et al. | |
| 5,382,685 A | 1/1995 | Klein et al. | |
| 5,382,885 A | 1/1995 | Salcudean et al. | |
| 5,389,100 A | 2/1995 | Bacich et al. | |
| 5,397,323 A | 3/1995 | Taylor et al. | |
| 5,397,340 A | 3/1995 | Nyman | |
| 5,398,691 A | 3/1995 | Martin | |
| 5,402,801 A | 4/1995 | Taylor | |
| 5,409,019 A | 4/1995 | Wilk | |
| 5,410,638 A | 4/1995 | Colgate et al. | |
| 5,417,210 A | 5/1995 | Funda et al. | |
| 5,429,144 A | 7/1995 | Wilk | |
| 5,437,290 A * | 8/1995 | Bolger et al. | 128/898 |
| 5,447,149 A | 9/1995 | Kikawada et al. | |
| 5,462,529 A | 10/1995 | Simpson et al. | |
| 5,477,856 A | 12/1995 | Lundquist | |
| 5,480,422 A | 1/1996 | Ben-Haim | |
| 5,492,131 A | 2/1996 | Galel | |
| 5,497,776 A | 3/1996 | Yamazaki et al. | |
| 5,497,784 A | 3/1996 | Imran | |
| 5,515,478 A | 5/1996 | Wang | |
| 5,515,851 A | 5/1996 | Goldstein | |
| 5,520,644 A | 5/1996 | Imran | |
| 5,524,180 A | 6/1996 | Wang et al. | |
| 5,540,649 A | 7/1996 | Bonnell et al. | |
| 5,553,198 A | 9/1996 | Wang et al. | |
| 5,572,999 A | 11/1996 | Funda et al. | |
| 5,606,979 A | 3/1997 | Hodgson | |
| 5,618,294 A | 4/1997 | Aust et al. | |
| 5,624,398 A | 4/1997 | Smith et al. | |
| 5,626,553 A | 5/1997 | Frassica et al. | |
| 5,626,595 A | 5/1997 | Sklar et al. | |
| 5,631,973 A | 5/1997 | Green | |
| 5,632,758 A | 5/1997 | Sklar | |
| 5,634,897 A | 6/1997 | Dance et al. | |
| 5,636,634 A | 6/1997 | Kordis et al. | |
| 5,649,956 A | 7/1997 | Jensen et al. | |
| 5,657,429 A | 8/1997 | Wang et al. | |
| 5,662,587 A | 9/1997 | Grundfest et al. | |
| 5,667,476 A | 9/1997 | Frassica et al. | |
| 5,667,490 A | 9/1997 | Keith et al. | |
| 5,674,279 A | 10/1997 | Wright et al. | |
| 5,713,946 A | 2/1998 | Ben-Haim | |
| 5,738,096 A | 4/1998 | Ben-Haim | |
| 5,749,362 A | 5/1998 | Funda | |
| 5,754,741 A | 5/1998 | Wang et al. | |
| 5,759,153 A | 6/1998 | Webler et al. | |
| 5,762,458 A | 6/1998 | Wang et al. | |
| 5,771,902 A | 6/1998 | Lee et al. | |
| 5,784,542 A | 7/1998 | Ohm et al. | |
| 5,791,908 A | 8/1998 | Gillio | |
| 5,792,135 A | 8/1998 | Madhani et al. | |
| 5,800,333 A | 9/1998 | Liprie | |
| 5,800,423 A | 9/1998 | Jensen | |
| 5,807,377 A | 9/1998 | Madhani et al. | |
| 5,808,665 A | 9/1998 | Green | |
| 5,810,880 A | 9/1998 | Jensen et al. | |
| 5,814,038 A | 9/1998 | Jensen et al. | |
| 5,815,640 A | 9/1998 | Wang | |
| 5,817,119 A | 10/1998 | Klieman et al. | |
| 5,821,920 A | 10/1998 | Rosenberg et al. | |
| 5,823,993 A | 10/1998 | Lemelson | |
| 5,825,982 A | 10/1998 | Wright et al. | |
| 5,827,313 A | 10/1998 | Ream | |
| 5,828,197 A | 10/1998 | Martin et al. | |
| 5,833,605 A | 11/1998 | Shah | |
| 5,833,608 A | 11/1998 | Acker | |
| 5,833,656 A | 11/1998 | Smith et al. | |
| 5,833,658 A | 11/1998 | Levy et al. | |
| 5,840,026 A | 11/1998 | Uber et al. | |
| 5,843,076 A | 12/1998 | Webster | |
| 5,845,646 A | 12/1998 | Lemelson | |
| 5,855,553 A | 1/1999 | Tajima et al. | |
| 5,855,583 A | 1/1999 | Wang et al. | |
| 5,860,992 A | 1/1999 | Daniel et al. | |
| 5,861,024 A | 1/1999 | Rashidi | |
| 5,868,755 A | 2/1999 | Kanner et al. | |
| 5,868,775 A | 2/1999 | Bircoll | |
| 5,876,325 A | 3/1999 | Mizuno | |
| 5,878,193 A | 3/1999 | Wang et al. | |
| 5,897,533 A * | 4/1999 | Glickman | 604/256 |
| 5,904,667 A | 5/1999 | Falwell | |
| 5,907,664 A | 5/1999 | Wang et al. | |
| 5,928,248 A | 7/1999 | Acker | |
| 5,931,832 A | 8/1999 | Jensen | |
| 5,950,629 A | 9/1999 | Taylor | |
| 5,954,692 A | 9/1999 | Smith et al. | |
| 5,957,941 A | 9/1999 | Ream | |
| 5,964,717 A | 10/1999 | Gottlieb et al. | |
| 5,971,976 A | 10/1999 | Wang et al. | |
| 5,976,122 A | 11/1999 | Madhani et al. | |
| 5,993,378 A * | 11/1999 | Lemelson | 600/109 |
| 5,996,346 A | 12/1999 | Maynard | |
| 6,001,108 A | 12/1999 | Wang et al. | |
| 6,004,269 A | 12/1999 | Crowley et al. | |
| 6,007,550 A | 12/1999 | Wang et al. | |
| 6,007,560 A | 12/1999 | Gottlieb et al. | |
| 6,024,695 A | 2/2000 | Taylor et al. | |
| 6,036,636 A | 3/2000 | Motoki et al. | |
| 6,063,095 A | 5/2000 | Wang et al. | |
| 6,072,154 A | 6/2000 | Maynard | |
| 6,080,170 A | 6/2000 | Nash et al. | |
| 6,080,181 A | 6/2000 | Jensen et al. | |
| 6,083,170 A | 7/2000 | Ben-Haim | |
| 6,096,004 A | 8/2000 | Meglan et al. | |
| 6,102,850 A | 8/2000 | Wang et al. | |
| 6,102,920 A | 8/2000 | Sullivan et al. | |
| 6,106,511 A | 8/2000 | Jensen | |
| 6,120,433 A | 9/2000 | Mizuno et al. | |
| 6,123,084 A * | 9/2000 | Jandak et al. | 128/898 |
| 6,126,635 A | 10/2000 | Simpson et al. | |
| 6,132,368 A | 10/2000 | Cooper | |

| | | |
|---|---|---|
| 6,132,441 A | 10/2000 | Grace |
| 6,156,005 A | 12/2000 | Theron |
| 6,171,234 B1 | 1/2001 | White et al. |
| 6,179,856 B1 | 1/2001 | Barbere |
| 6,197,017 B1 | 3/2001 | Brock et al. |
| 6,206,868 B1 | 3/2001 | Parodi |
| 6,206,903 B1 | 3/2001 | Ramans |
| 6,221,070 B1 | 4/2001 | Tu et al. |
| 6,223,100 B1 | 4/2001 | Green |
| 6,231,565 B1 | 5/2001 | Tovey et al. |
| 6,233,474 B1 | 5/2001 | Lemelson |
| 6,233,476 B1 | 5/2001 | Strommer |
| 6,233,504 B1 | 5/2001 | Das et al. |
| 6,236,432 B1 | 5/2001 | Lee |
| 6,246,200 B1 | 6/2001 | Blumenkranz et al. |
| 6,266,551 B1 | 7/2001 | Osadchy |
| 6,267,781 B1 | 7/2001 | Tu |
| 6,269,819 B1 | 8/2001 | Oz et al. |
| 6,272,371 B1 | 8/2001 | Ben-Haim |
| 6,283,921 B1 | 9/2001 | Nix et al. |
| 6,290,675 B1 | 9/2001 | Vujanic et al. |
| 6,292,681 B1 | 9/2001 | Moore |
| 6,293,282 B1 * | 9/2001 | Lemelson ............... 128/899 |
| 6,295,989 B1 | 10/2001 | Connors, III |
| 6,297,611 B1 | 10/2001 | Todorov et al. |
| 6,298,257 B1 | 10/2001 | Hall et al. |
| 6,309,397 B1 | 10/2001 | Julian et al. |
| 6,312,435 B1 | 11/2001 | Wallace et al. |
| 6,319,227 B1 | 11/2001 | Mansouri-Ruiz |
| 6,325,808 B1 | 12/2001 | Bernard et al. |
| 6,331,181 B1 | 12/2001 | Tierney et al. |
| 6,332,889 B1 | 12/2001 | Sancoff et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,366,830 B2 | 4/2002 | Bacchi et al. |
| 6,369,834 B1 | 4/2002 | Zilles et al. |
| 6,370,411 B1 | 4/2002 | Osadchy |
| 6,371,907 B1 | 4/2002 | Hasegawa et al. |
| 6,371,952 B1 | 4/2002 | Madhani |
| 6,375,471 B1 | 4/2002 | Wendlandt et al. |
| 6,377,011 B1 | 4/2002 | Ben-Ur |
| 6,385,509 B2 | 5/2002 | Das et al. |
| 6,393,340 B2 | 5/2002 | Funda |
| 6,394,998 B1 | 5/2002 | Wallace et al. |
| 6,397,323 B1 | 5/2002 | Yoshida |
| 6,398,726 B1 | 6/2002 | Ramans et al. |
| 6,398,755 B1 | 6/2002 | Belef et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,451,027 B1 | 9/2002 | Cooper et al. |
| 6,459,926 B1 | 10/2002 | Nowlin et al. |
| 6,463,361 B1 | 10/2002 | Wang et al. |
| 6,468,265 B1 | 10/2002 | Evans et al. |
| 6,485,482 B1 | 11/2002 | Belef |
| 6,485,489 B2 | 11/2002 | Teirstein et al. |
| 6,490,490 B1 | 12/2002 | Uchikubo et al. |
| 6,491,691 B1 | 12/2002 | Morley et al. |
| 6,491,701 B2 | 12/2002 | Tierney et al. |
| 6,493,608 B1 | 12/2002 | Niemeyer et al. |
| 6,496,099 B2 | 12/2002 | Wang et al. |
| 6,517,565 B1 | 2/2003 | Whitman et al. |
| 6,522,906 B1 | 2/2003 | Salisbury, Jr. et al. |
| 6,554,844 B2 | 4/2003 | Lee et al. |
| 6,565,554 B1 | 5/2003 | Niemeyer |
| 6,569,084 B1 | 5/2003 | Mizuno |
| 6,574,355 B2 | 6/2003 | Green |
| 6,587,750 B2 | 7/2003 | Gerbi et al. |
| 6,594,552 B1 | 7/2003 | Nowlin et al. |
| 6,610,007 B2 | 8/2003 | Belson |
| 6,620,173 B2 | 9/2003 | Gerbi et al. |
| 6,626,899 B2 | 9/2003 | Houser |
| 6,645,196 B1 | 11/2003 | Nixon et al. |
| 6,659,939 B2 | 12/2003 | Moll |
| 6,669,687 B1 | 12/2003 | Saadat |
| 6,676,684 B1 | 1/2004 | Morley et al. |
| 6,685,698 B2 | 2/2004 | Morley et al. |
| 6,692,485 B1 | 2/2004 | Brock et al. |
| 6,699,235 B2 | 3/2004 | Wallace et al. |
| 6,702,826 B2 | 3/2004 | Liddicoat et al. |
| 6,720,988 B1 | 4/2004 | Gere et al. |
| 6,726,675 B1 | 4/2004 | Beyar |
| 6,726,699 B1 | 4/2004 | Wright et al. |
| 6,728,599 B2 | 4/2004 | Wang et al. |
| 6,770,081 B1 | 8/2004 | Cooper et al. |
| 6,783,524 B2 | 8/2004 | Anderson et al. |
| 6,788,018 B1 | 9/2004 | Blumenkranz et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,817,972 B2 | 11/2004 | Snow |
| 6,817,973 B2 | 11/2004 | Merril et al. |
| 6,817,974 B2 | 11/2004 | Cooper et al. |
| 6,837,883 B2 | 1/2005 | Moll et al. |
| 6,840,938 B1 | 1/2005 | Morley et al. |
| 6,852,107 B2 | 2/2005 | Wang et al. |
| 6,858,003 B2 | 2/2005 | Evans |
| 6,860,877 B1 | 3/2005 | Sanchez et al. |
| 6,905,460 B2 | 6/2005 | Wang |
| 6,911,916 B1 | 6/2005 | Wang et al. |
| 6,936,001 B1 | 8/2005 | Snow |
| 6,936,056 B2 | 8/2005 | Nash et al. |
| 6,951,535 B2 | 10/2005 | Ghodoussi et al. |
| 6,963,792 B1 | 11/2005 | Green |
| 6,994,708 B2 | 2/2006 | Manzo |
| 7,025,064 B2 | 4/2006 | Wang et al. |
| 7,074,179 B2 | 7/2006 | Wang |
| 7,087,049 B2 | 8/2006 | Nowlin |
| 7,090,683 B2 | 8/2006 | Brock et al. |
| 7,214,230 B2 | 5/2007 | Brock et al. |
| 7,320,700 B2 | 1/2008 | Cooper |
| 7,331,967 B2 | 2/2008 | Lee et al. |
| 7,343,195 B2 | 3/2008 | Strommer |
| 7,371,210 B2 | 5/2008 | Brock |
| 7,727,185 B2 * | 6/2010 | Weitzner et al. ............ 604/95.01 |
| 2002/0087151 A1 | 7/2002 | Mody et al. |
| 2002/0087166 A1 | 7/2002 | Brock et al. |
| 2003/0135204 A1 | 7/2003 | Lee |
| 2004/0034282 A1 | 2/2004 | Quaid |
| 2004/0034365 A1 | 2/2004 | Lentz |
| 2005/0059930 A1 | 3/2005 | Garrison et al. |
| 2006/0200049 A1 | 9/2006 | Leo |
| 2007/0060847 A1 | 3/2007 | Leo |
| 2007/0250074 A1 * | 10/2007 | Brock et al. ................. 606/130 |
| 2007/0293724 A1 | 12/2007 | Saadat |
| 2008/0009750 A1 | 1/2008 | Aeby |
| 2008/0015445 A1 | 1/2008 | Saadat |
| 2008/0300592 A1 | 12/2008 | Weitzner |

FOREIGN PATENT DOCUMENTS

| | | |
|---|---|---|
| EP | 0776738 | 4/1997 |
| WO | WO 93/14704 | 5/1993 |
| WO | WO 98/25666 | 6/1998 |
| WO | WO 00/60521 | 10/2000 |
| WO | WO 00/67640 | 11/2000 |
| WO | WO 02/74178 | 2/2002 |
| WO | WO 03-091839 | 11/2003 |

OTHER PUBLICATIONS

M.W. Thring, "Robots and Telechirs: Manipulators With Memory; Remote Manipulators, Machine Limbs for the Handicapped", First published in 1983 by Ellis Horwood Limited.

Documents from File history for related U.S. Appl. No. 11/467,886, filed Aug. 28, 2006, Applicant Hansen Medical, including: Non Final Rejection for U.S. Appl. No. 11/467,886, dated Apr. 30, 2008. Response to Non Final Rejection for U.S. Appl. No. 11/467,886 dated Apr. 30, 2008, response submitted on Jul. 30, 2008. Final Rejection for U.S. Appl. No. 11/467,886, dated Oct. 24, 2008. Amendment and Response to Final Rejection for U.S. Appl. No. 11/467,886, dated Oct. 24, 2008, response submitted on Jan. 26, 2009. Advisory Action for U.S. Appl. No. 11/467,886, dated Feb. 13, 2009. Appeal Brief submitted for U.S. Appl. No. 11/467,886, submitted on Apr. 20, 2009. (50 pages total).

Documents from File history for related U.S. Appl. No. 11/762,751, filed Jun. 13, 2007, Applicant Hansen Medical, including: Non Final Rejection for U.S. Appl. No. 11/762,751, dated Apr. 15, 2009. (10 pages).

Documents from File history for related U.S. Appl. No. 11/762,748, filed Jun. 13, 2007, Applicant Hansen Medical, including: Non Final Rejection for U.S. Appl. No. 11/762,748, dated Apr. 2, 2009. (15 pages).

Documents from File history for related U.S. Appl. No. 12/023,943, filed Jan. 31, 2008, Applicant Hansen Medical, including: Non Final Rejection for U.S. Appl. No. 12/023,943, dated Nov. 19, 2008. Response to Non Final Rejection for U.S. Appl. No. 12/023,943, dated Nov. 19, 2009, submitted on Feb. 19, 2009. Final Rejection for U.S. Appl. No. 12/023,943, dated May 22, 2009. (26 pages total).

Documents from File history for related U.S. Appl. No. 11/467,886, filed Aug. 28, 2006, Applicant Barry Weitzner et al., including: Examiner's Answer to the Appeal Brief submitted Apr. 20, 2009, Answer mailed Jun. 29, 2009 Amendment submitted with RCE, submitted on Aug. 27, 2009 Non-final rejection dated Nov. 9, 2009 Amendment response to non final rejection dated Nov. 9, 2009, response submitted on Feb. 8, 2010 Final rejection dated Apr. 27, 2010 Amendment response to final rejection dated Apr. 27, 2010, response submitted on May 3, 2010 (57 pages total).

Documents from File history for related U.S. Appl. No. 11/762,751, filed Jun. 13, 2007, Applicant Barry Weitzner et al., including: Amendment response to Non Final Rejection dated Apr. 15, 2009, response submitted on Jul. 15, 2009; Supplemental response to Non Final Rejection dated Apr. 15, 2009, response submitted on Jul. 21, 2009; Final rejection dated Nov. 10, 2009; Amendment submitted with RCE in response to Final Rejection dated Nov. 10, 2009, response submitted Feb. 10, 2010; Supplemental response submitted in response to Final Rejection dated Nov. 10, 2009, response submitted Feb. 26, 2010; Non Final Rejection dated Apr. 19, 2010; Amendment response to Non Final Rejection dated Apr. 19, 2010, response submitted on Apr. 20, 2010; Non Final Rejection dated Jun. 30, 2010; Amendment response to Non Final Rejection dated Jun. 30, 2010, response submitted on Nov. 1, 2010; (115 pages total).

Documents from File history for related U.S. Appl. No. 11/762,748, filed Jun. 13, 2007, Applicant Barry Weitzner et al., including: Amendment response to Non Final Rejection dated Apr. 2, 2009, response submitted Jul. 2, 2009; Final Rejection dated Oct. 29, 2009; Amendment response to Final Rejection dated Oct. 29, 2009, response submitted on Nov. 4, 2009; (42 pages total).

Documents from File history for related U.S. Appl. No. 12/023,943, filed Jan. 31, 2008, Applicant Barry Weitzner et al., including: Amendment submitted with RCE in response to Final Rejection dated May 22, 2009, response submitted on Aug. 10, 2009; Non Final Rejection dated Nov. 16, 2009; Amendment response to Non Final Rejection dated Nov. 16, 2009, response submitted on Apr. 15, 2010; Final Rejection dated Jun. 28, 2010; Amendment submitted with RCE in response to Final Rejection dated Jun. 28, 2010 (51 pages).

* cited by examiner

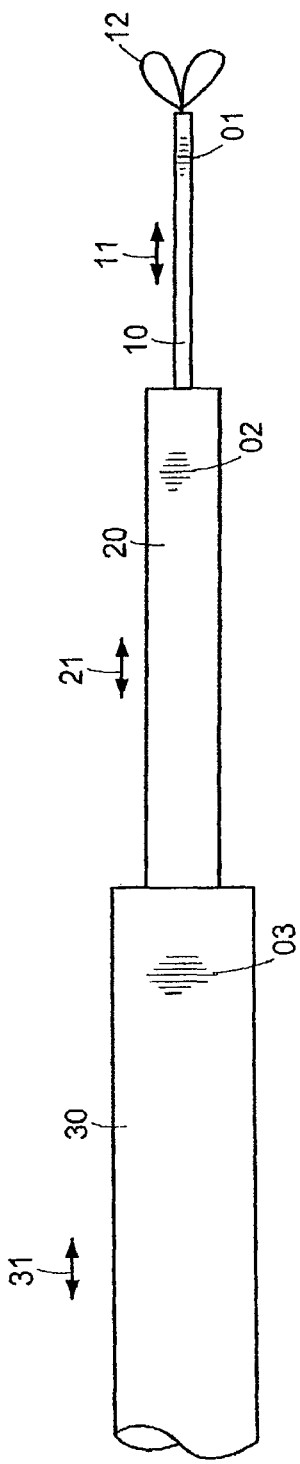
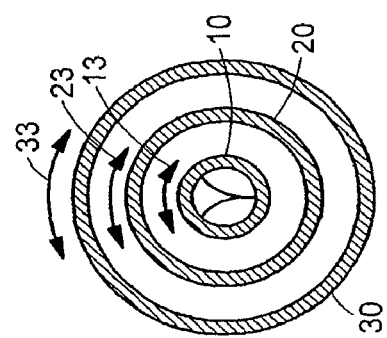
FIG. 2A
FIG. 2B

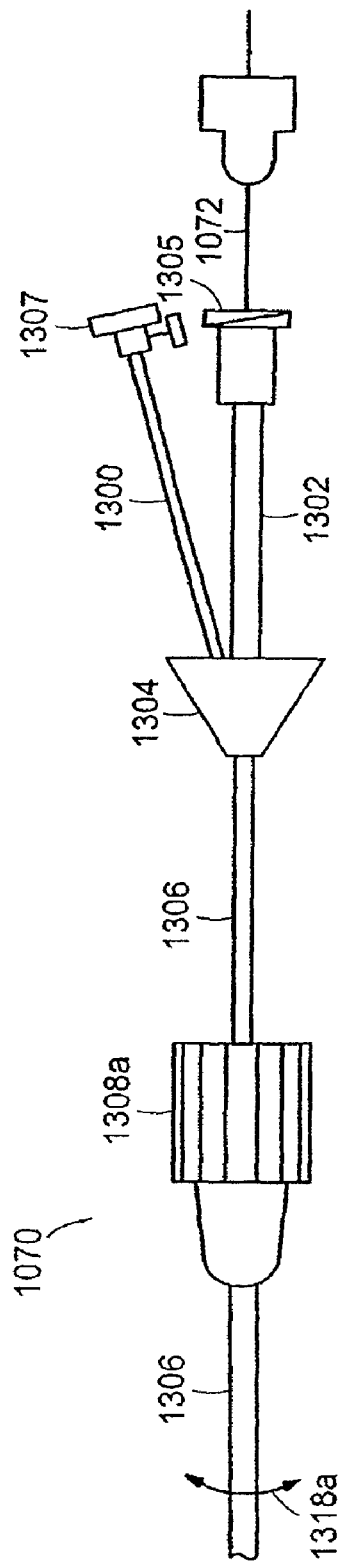
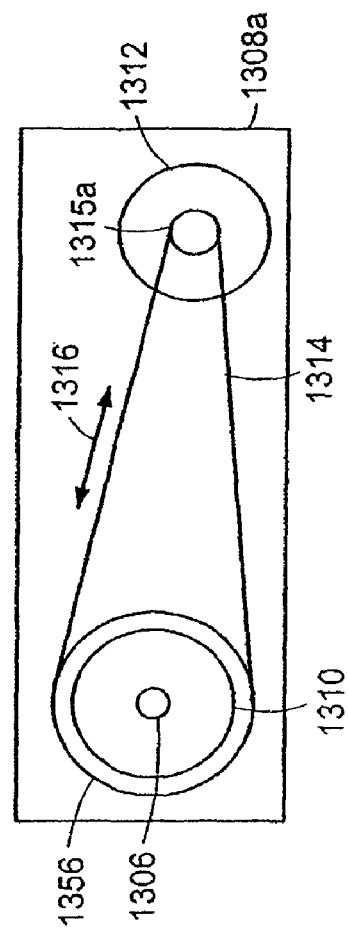
FIG. 12
FIG. 12A

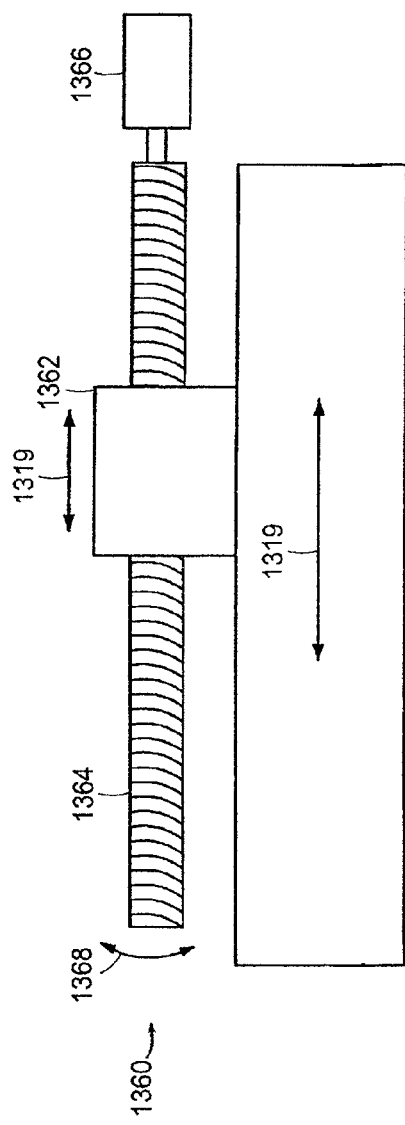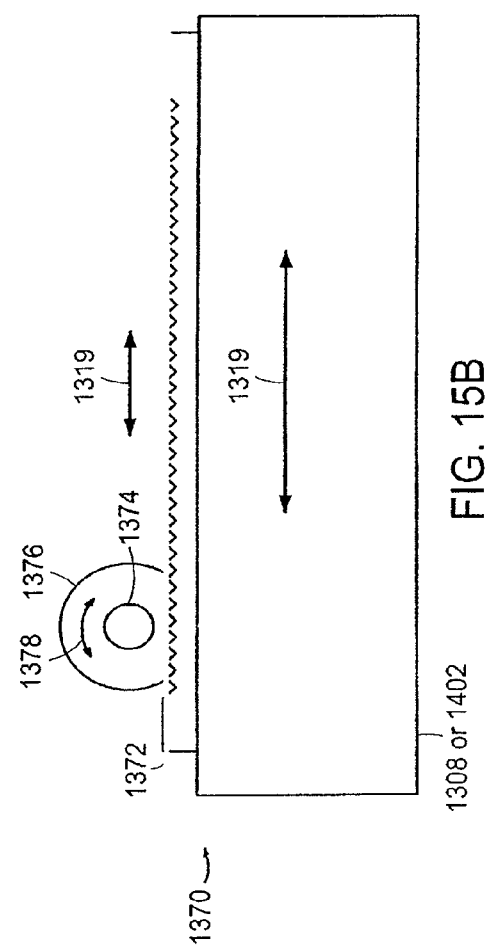

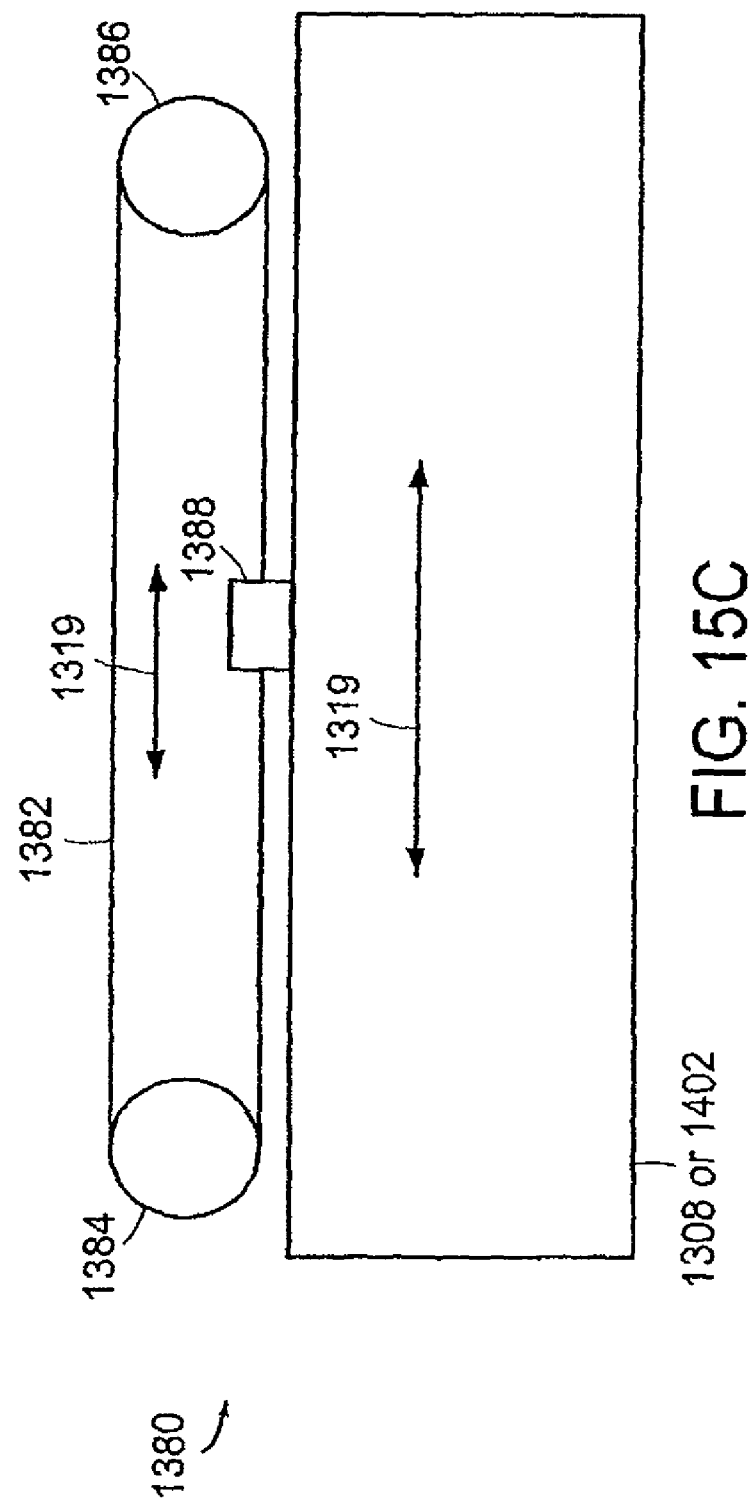

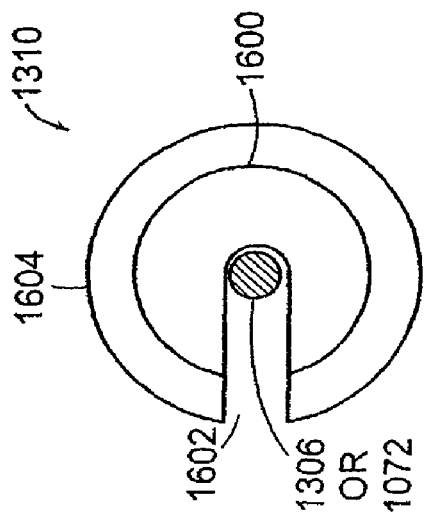
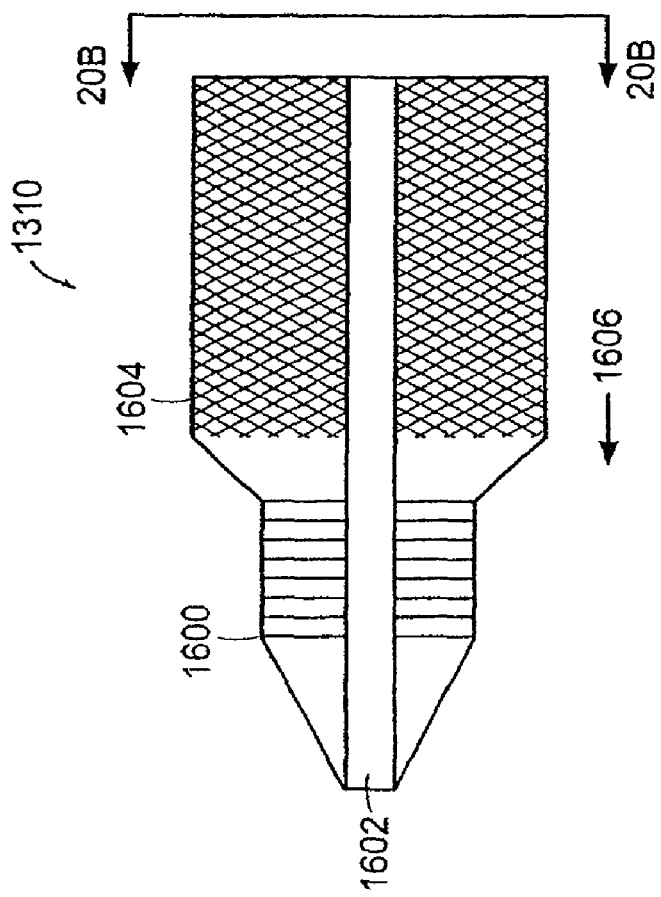
FIG. 20B
FIG. 20A

COAXIAL CATHETER SYSTEM

RELATED APPLICATIONS

This application is a continuation of U.S. application Ser. No. 11/467,886, filed Aug. 28, 2006, which is a continuation of U.S. application Ser. No. 10/270,740, filed Oct. 11, 2002 (now abandoned), which claims the benefit of U.S. application Ser. No. 60/332,287, filed Nov. 21, 2001, and is a continuation-in-part of U.S. application Ser. No. 10/216,069, filed Aug. 8, 2002, which claims the benefit of U.S. application Ser. No. 60/313,495, filed Aug. 21, 2001, and is a continuation-in-part of U.S. application Ser. Nos. 10/023,024 (now abandoned), 10/011,371 (now U.S. Pat. No. 7,090,683), 10/011,449 (now abandoned), 10/010,150 (now U.S. Pat. No. 7,214,230), 10/022,038 (now abandoned), and 10/012,586, all filed Nov. 16, 2001, and all of which claim the benefit of U.S. application Ser. Nos. 60/269,200, filed Feb. 15, 2001, 60/276,217, filed Mar. 15, 2001, 60/276,086, filed Mar. 15, 2001, 60/276,152, filed Mar. 15, 2001, and 60/293,346, filed May 24, 2001.

This application is also related to U.S. application Ser. Nos. 11/762,751 and 11/762,748, all of which are filed on Jun. 13, 2007. The entire disclosures of the above applications are expressly incorporated herein by reference.

BACKGROUND OF THE INVENTION

Catheters are used extensively in the medical field in various types of medical procedures, as well as other invasive procedures. In general, minimally invasive medical procedures involve operating through a natural body opening or orifice of a body lumen, or through small incisions, typically 5 mm to 10 mm in length, through which instruments are inserted. In general, minimally invasive surgery is less traumatic than conventional surgery, due, in part, because no incision is required in certain minimally invasive procedures, or the significant reduction in the incision size in other procedures. Furthermore, hospitalization is reduced and recovery periods are shortened as compared with conventional surgical techniques.

Catheters maybe provided in a variety of different shapes and sizes depending upon the particular application. It is typical for a clinician to manipulate the proximal end of the catheter to guide the distal end of the catheter inside the body, for example, through a vein or artery. Because of the small size of the incision or opening and the remote location of the distal end of the catheter, much of the procedure is not directly visible to the clinician. Although clinicians can have visual feedback from the procedure site through the use of a video camera or endoscope inserted into the patient, or through radiological imaging or ultrasonic imaging, the ability to control even relatively simple instruments remains difficult.

In view of the above, some have proposed using robotic tele-surgery to perform minimally invasive procedures. Typically, these robotic systems use arms that reach over the surgical table and manipulate the surgical instruments inserted into the patient, while the surgeon sits at a master station located a distance from the table and issues commands to the arms.

SUMMARY OF THE INVENTION

In accordance with the present inventions, a medical system comprises a first medical probe (e.g., a flexible catheter) having indicia, and a second medical probe (e.g., a flexible catheter) in a coaxial arrangement with the first medical probe. The second medical probe has a detector (e.g., an optical detector) configured for detecting a passage of the indicia as the first and second medical probes are moved relative to each other. In one embodiment, the first medical probe is an inner medical probe, and the second medical probe is an outer medical probe. The medical system further comprises an electromechanical driver coupled to the first and second medical probes, and a controller configured for directing the electromechanical driver to move the first and second medical probes relative to each other, and for receiving signals from the detector indicating the relative movement between the first and second medical probes. In one embodiment, the first medical probe further includes an articulating tool, in which case, the controller may be configured for directing the electromechanical driver to actuate the articulating tool. In another embodiment, the controller is coupled to the electromechanical driver via external cabling. In still another embodiment, the medical system further comprises a user interface configured for receiving at least one command, in which case, the controller may be configured for directing the electromechanical driver in response to the command(s).

The controller can control relative movement between the first and second medical probes based on the detected indicia. For example, the controller may be configured for directing the electromechanical driver to linearly translate the first and second medical probes relative to each other. In this case, the indicia may be disposed along a length of the first medical probe, the detector may be configured for detecting a linear passage of the indicia as the first and second medical probes are linearly translated relative to each other, and the controller may be configured for receiving signals from the detector indicating the relative linear translation between the first and second medical probes. As another example, the controller may be configured for directing the electromechanical driver to axially rotate the first and second medical probes relative to each other. In this case, the indicia may be disposed along a circumference of the first medical probe, the detector may be configured for detecting a rotational passage of the indicia as the first and second medical probes are axially rotated relative to each other, and the controller may be configured for receiving signals from the detector indicating the relative axial rotation between the first and second medical probes.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2A is a side view of the coaxial catheter system of FIG. 1;

FIG. 2B is a cross-sectional view of the catheter system illustrated in FIG. 2A;

FIG. 12 illustrates a catheter coupled to a catheter drive mechanism in accordance with the invention;

FIG. 12A is a cross-sectional view of the drive mechanism of FIG. 12;

FIGS. 15A-15C illustrate various devices used to move the drive mechanisms of FIG. 13 in a linear manner;

FIGS. 20A and 20B illustrate yet another embodiment of the connector.

DETAILED DESCRIPTION OF THE INVENTION

Figure 1:
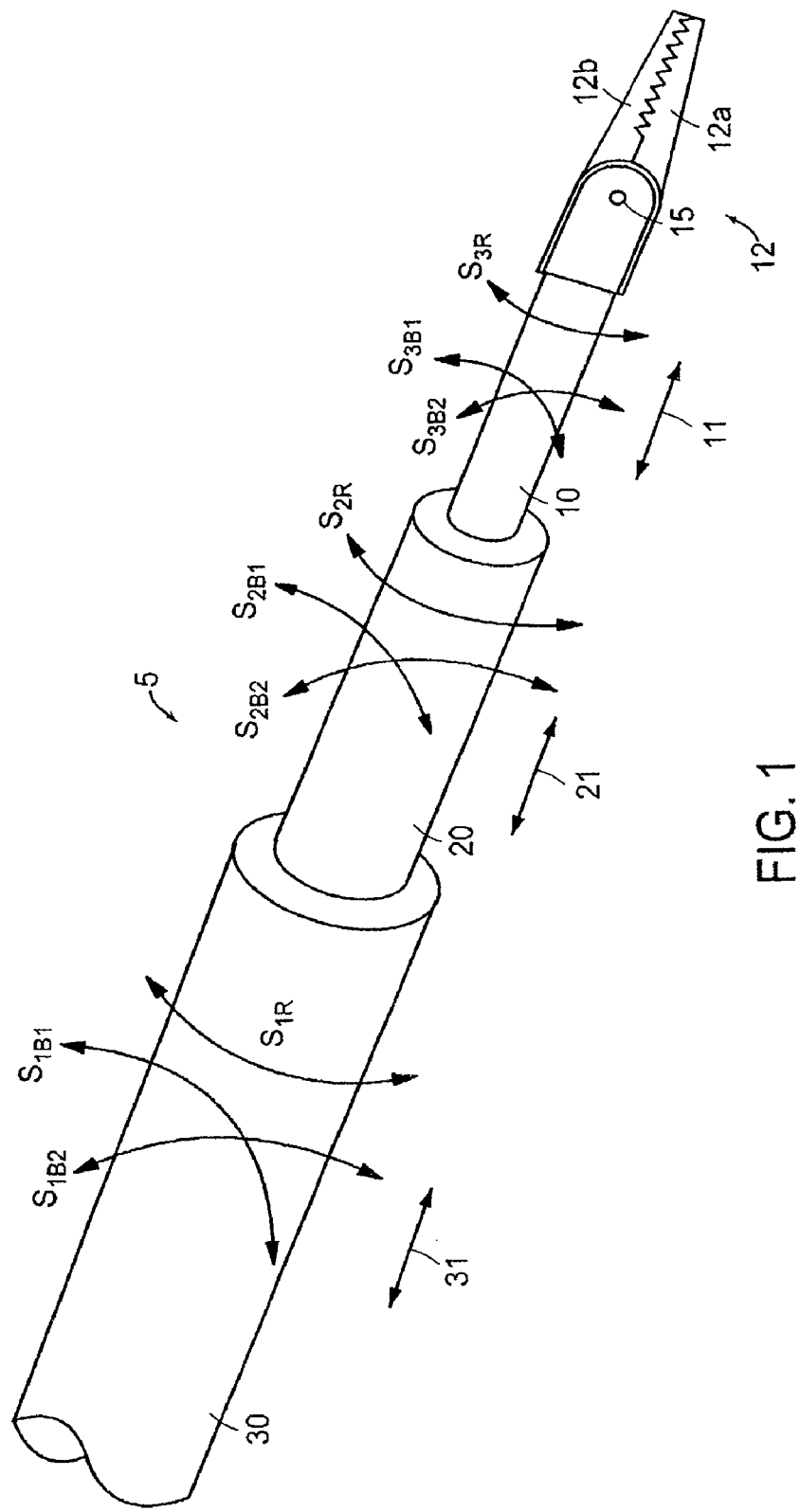
FIG. 1 is a schematic perspective view of a coaxial catheter in accordance with the present invention.

A description of preferred embodiments of the invention follows. Referring to FIG. 1 there is shown a catheter system 5 including three separate catheter shafts 10, 20, and 30, with an end effector 12 supported at the distal end of the catheter shaft 10. The end effector 12 may be, for example, an articulated tool such a grasper with a pair of jaws 12a and 12b that pivot about a joint 15 to grasp an item between the two jaw members. Other articulated tools that may be used as the end effector 12 include scissors, needle holders, micro dissectors, staple appliers, tackers, suction irrigation tools, and clip appliers. The end effector 12 can also be a non-articulated tool, such as a cutting blade, probe, irrigator, catheter or suction orifice, and dilation balloon. Further details of catheter systems, particularly those relating to mechanisms for multiple degrees-of-freedom of motion of catheter shafts can be found in U.S. application Ser. Nos. 10/023,024, 10/011,449, 10/022,038, 10/012,586, by Brock, Lee, Weitzner and Rogers, Ser. No. 10/011,371, by Brock, Lee, Weitzner, Rogers, and Ailenger, and Ser. No. 10/010,150, by Brock, Lee, Weitzner, Rogers, and Cunningham, all of which were filed Nov. 16, 2001 and are incorporated herein by reference in their entirety.

Each of the catheter shafts 10, 20, and 30 has a different diameter that is able to move with multiple degrees-of-freedom. The catheter shafts shown in FIG. 1 are arranged in a coaxial manner with the small diameter catheter 10 positioned inside the medium diameter catheter 20 which in turn is positioned inside the large catheter 30. The arrangement in FIG. 1 is a coaxial arrangement with the small diameter catheter 10 adapted for sliding inside of the medium diameter catheter 20.

As illustrated in FIG. 1, as well as FIG. 2A, the catheter 30 is able to move with a linear translation in the direction 31, while the medium diameter catheter 20 is able to slide inside the catheter 30 with a linear translation motion in the direction 21, and the small catheter 10 is able to slide inside the medium catheter with a linear translation motion in the direction 11.

In addition to the translation motions, each of the catheter shafts 10, 20, and 30 is able to rotate and bend. Hence, the shafts 10, 20, and 30 have three degrees-of-freedom of movement. The rotational motion of the catheters 10, 20, and 30 is indicated by the double arrows $S_{3R}$, $S_{2R}$ and $S_{1R}$, respectively, and the orthogonal bending motions of the catheters 10, 20, and 30 are indicated by the double arrows $S_{3B1}$ and $S_{3B2}$, $S_{2B1}$ and $S_{2B2}$ and $S_{1B1}$ and $S_{1B2}$.

Referring also to FIG. 2B, there is shown the coaxial arrangement of the catheters 10, 20, and 30, as well as the rotational motions of the catheters identified by the double arrows 13, 23, and 33, respectively. Indicated in FIG. 2A are the operative segments 01, 02, and 03 of the respective catheters 10, 20, and 30 where the bending may occur in each of the catheters. As shown, this bending generally occurs near the distal end of the respective catheters. However, the operative segments may also be located at different places along each of the catheters or may not be required at all.

Figure 3:
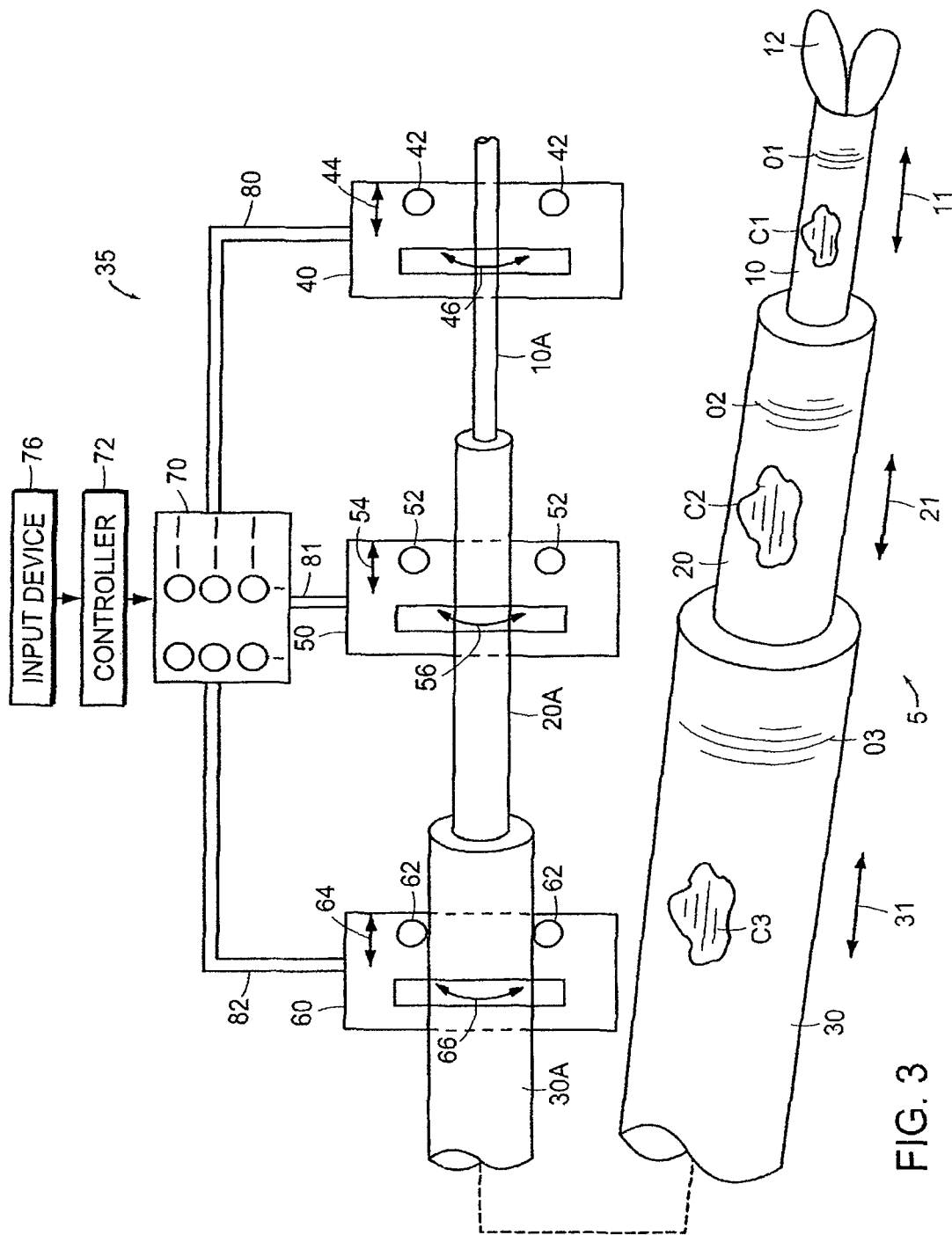
FIG. 3 is a schematic and block diagram of the coaxial catheter system in accordance with the present invention.

Turning now to FIG. 3, the multiple coaxial catheters 10, 20, and 30 are shown coupled to a drive system 35. Also shown in FIG. 3 are the operative sections 01, 02, and 03 of the catheters 10, 20, and 30, respectively, as well as the linear translational degree-of-freedom 11, 21, and 31. At some position along the catheters, there is a patient interface, not specifically illustrated in FIG. 3 but considered to be the location where the catheter enters the anatomic body. The entry of the catheter may, for example, be percutaneously, via an incision, or even through a natural body orifice. Procedures to be described below are particularly adapted for transitioning a multi-shaft catheter constriction through an anatomic body vessel such as through the intestines. Of course, the concepts of the illustrated embodiments may be used in association with the control and transition of the catheters through other body vessels or body cavities as well.

Each catheter 10, 20, and 30 is arranged and supported in a manner to enable multiple degrees-of-freedom of the catheter including movement of the catheter to an anatomic body target site, as well as rotation of the catheter. In particular, there are respective support blocks 40, 50, and 60 associated with the catheters 10, 20, and 30. In the embodiment illustrated in FIG. 3, these support blocks 40, 50, and 60 are coupled to the respective proximal ends of the catheters identified as 10A, 20A, and 30A. Each of the support blocks controls linear translational movements of the catheters with the use of wheels 42, 52, and 62. In support block 40, there is also illustrated control of the rotational motion 46 of the catheter 10. Similarly, support blocks 50 and 60 provide rotational control 56 and 66 to the respective catheters 50 and 60.

The drive system 35 also includes an electromechanical drive member 70 coupled to the support blocks 40, 50, and 60 with mechanical cablings 80, 81, and 82, respectively. The drive member 70 is a under the direction of a controller 72 that is also coupled to an input device 76 which interfaces the drive system 35, and hence the catheter system 5, with a user who is typically a surgeon.

In the illustrated embodiment, the electromechanical drive member 70 is a motor array with a plurality of drive motors. The mechanical cablings 80, 81, and 82 provide control of the respective blocks and controls the linear and rotational movement of the respective catheters. Thus, in the motor array 70, there can be at least one motor for controlling linear translation, and a separate motor for controlling rotational translation relative to each of the support blocks.

Thus, when the system 35 is in use, the surgeon provides instructions to the controller 72 through the input device 72. In turn, the controller 72 directs the operation of the motor array 70 and hence the support blocks 40, 50, and 60 which drive the respective catheters with multiple degrees-of-freedom of movement.

The motor array 70 also includes separate motors for driving the bending movements $S_{3B1}$ and $S_{3B2}$, $S_{2B1}$ and $S_{2B2}$ and $S_{1B1}$, and $S_{1B2}$ of the catheters as previously indicated in FIG. 1. In FIG. 3, in addition to the operative segments 01, 02, and 03 where the bending of the individual catheter occurs, there are also shown in cut-out cross-section in each of the catheters respective cablings C1, C2, and C3. These cablings extend along the length of the respective catheters and can be used for controlling the bending of the operative segments. Also, cabling that extends through catheters 10, 20, and 30 can be used to operate the end effector 12 as well. The cabling C1, C2, and C3 can extend through the catheters and through the corresponding support blocks, coupling through the various mechanical cablings 80, 81, and 82. Accordingly, there may be control motors in the motor array 70 that control the bending movements of the catheters, as well as operation of the end effector 12. Further details of mechanical cabling used for the operation of catheters including bending and flexing thereof can be found in the U.S. application Ser. Nos. 10/023,024, 10/011,371, 10/011,449, 10/010,150, 10/022,038, and 10/012,586 mentioned earlier.

In some embodiments, the controller 72 is a microprocessor that receives input commands from the input device 76. The input device 76 can be one of various types of controls such as a dial, joystick, wheel, or mouse. A touch-screen can also be employed as the input device 76 to allow the surgeon to input information about the desired location of a particular portion of the catheter by touching the screen. In this regard, reference may also be made to the U.S. application entitled "Catheter Tracking System," by Weitzner and Lee, U.S. application Ser. No. 10/216,669, filed herewith, the entire contents of which are incorporated herein by reference, which describes a catheter tracking system that enables an operator at the input device to select a particular anatomic body site and direct the catheter automatically to that site.

Figure 4:
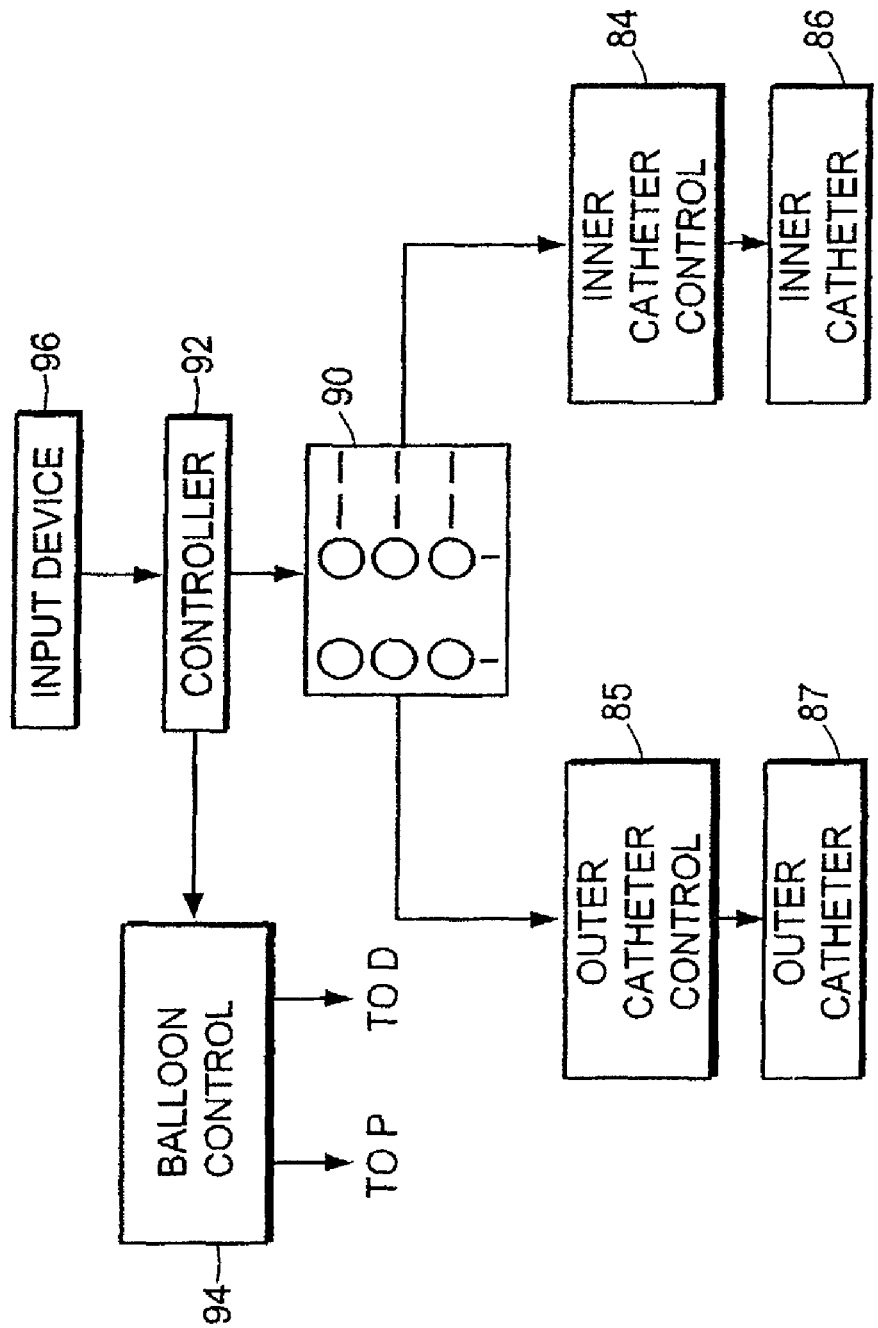
FIG. 4 is a block diagram of another embodiment of the present invention employing controllable balloons for controlled movement of the coaxial catheter system.
Figure 5:
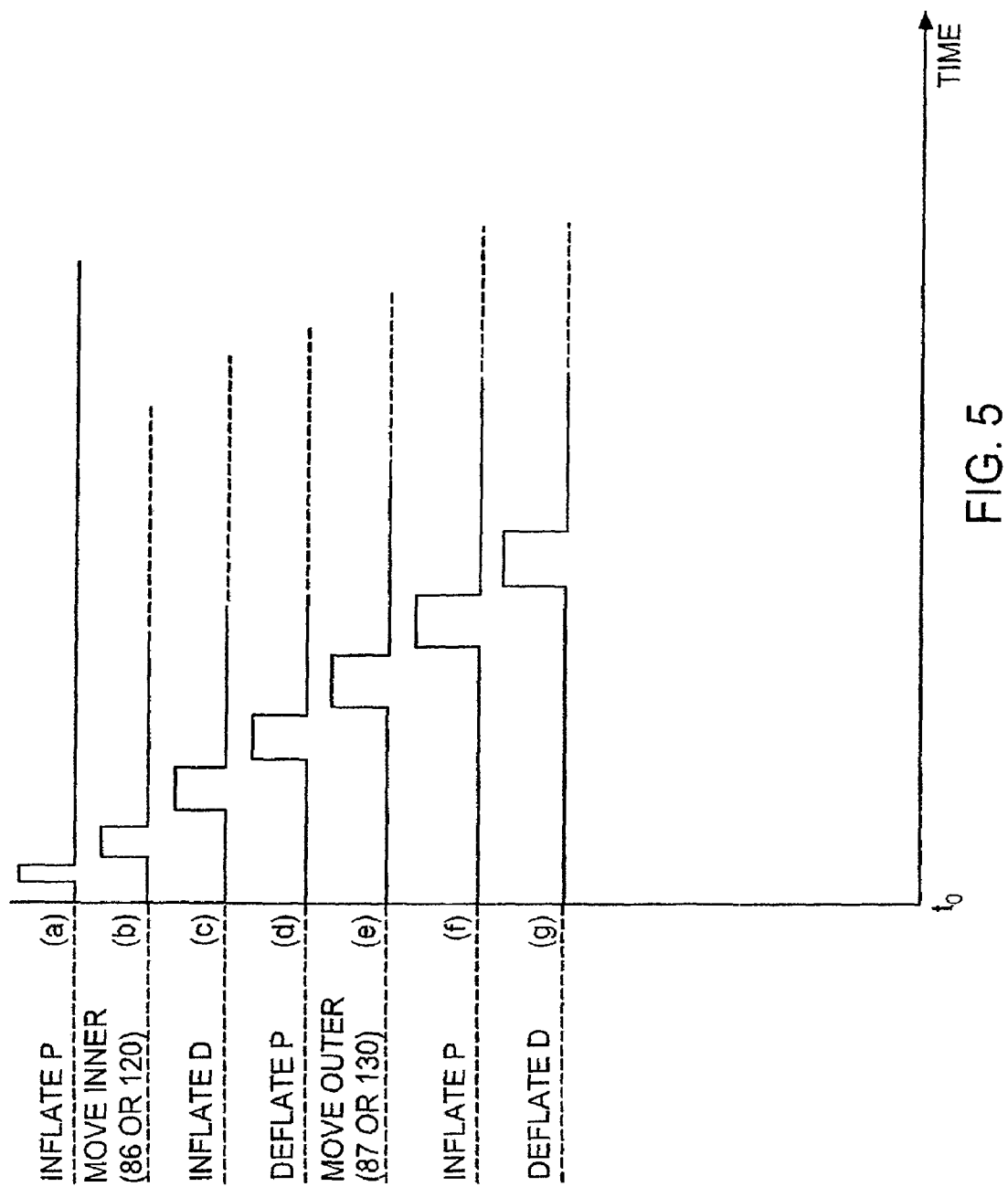
FIG. 5 is a timing diagram associated with the block diagram of FIG. 4.
Figure 6:
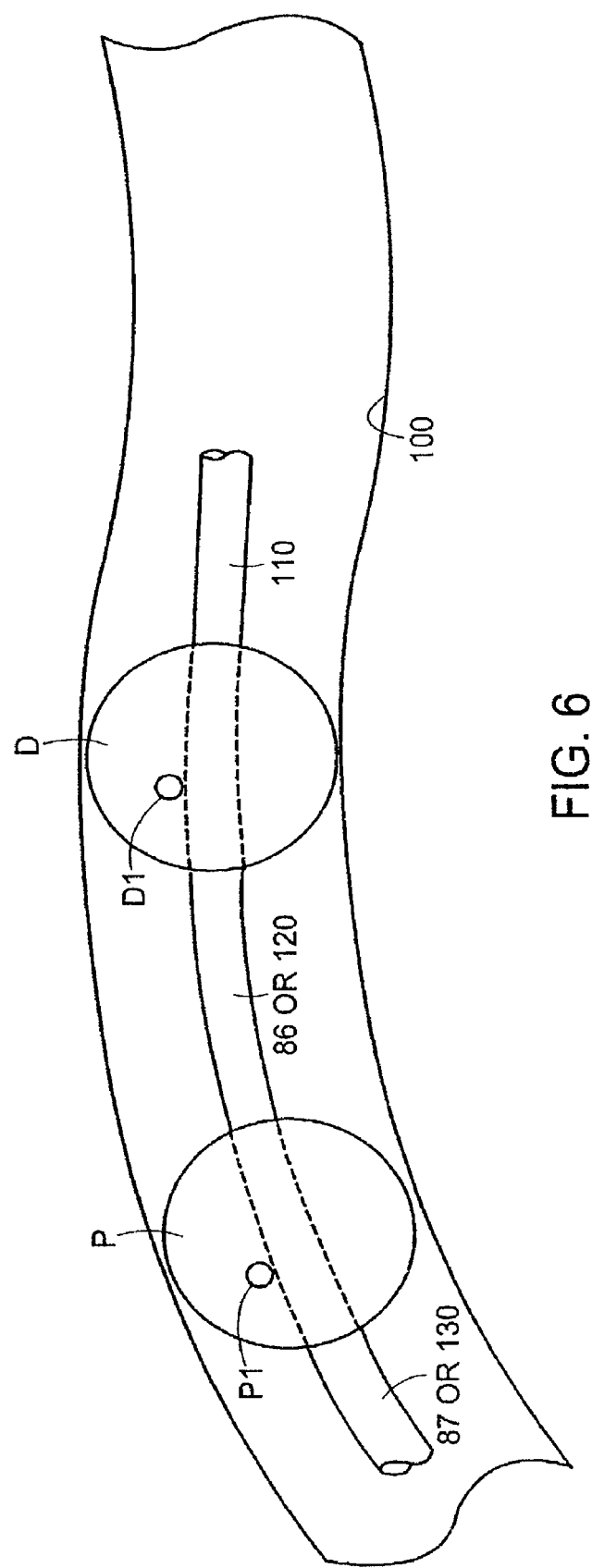
FIG. 6 is a schematic diagram illustrating the coaxial catheter arrangement and associated proximal and distal balloons, associated with the block diagram of FIG. 4.

Referring to FIGS. 4, 5 and 6, there is shown another implementation of the catheter control. Here, the system employs multiple catheters with multiple balloons in combination with a control mechanism by which the balloons are inflated and deflated to move the catheters in increments through a body vessel. In FIG. 6, a set of catheters 110, 120, and 130 are located within a body vessel 100. Associated with catheter 120 is a distal balloon D. and similarly, associated with the distal end of catheter 130 is a proximal balloon P. In FIG. 6 there are also shown ports D1 and P1 through which air or other fluid is introduced into each of the balloons to inflate the balloons or removed to deflate the balloons. In FIG. 6 the proximal balloon P is shown inflated and the distal balloon D is shown deflated. Note that although only two balloons are shown, one or more additional balloons can be associated with a third or even a fourth catheter.

In the block diagram of FIG. 4 there is identified an inner catheter 86 and an outer catheter 87, which may correspond respectively to catheters 120 and 130 in FIG. 6. Also illustrated in FIG. 4 is an inner catheter control 84 and an outer catheter control 85. These controls may be similar to the controls illustrated in FIG. 3 for at least controlling the advancement in a linear manner of the corresponding catheter. Thus, the catheter control 84 can be considered as controlling the linear movement of the inner catheter 86 while the catheter control 85 can be considered as controlling the linear translation of the outer catheter 87.

The outputs of a motor array 90 are coupled to the inner catheter control 84 and the outer catheter control 85, while a controller 92 is coupled to and controls the motor any 90. An input device 96 connected to the controller 92 provides an interface for a user such as surgeon to operate the inner and outer catheters 86 and 87.

Also illustrated in FIG. 4 is a balloon controller 94 associated with the controller 92 and that has two separate outputs coupled to the proximal, P, and distal, D, balloons. Under the direction of the controller 92 the balloon controller controls the inflation and deflation of the proximal balloon P and the distal balloon D. Details about the timing of the inflation and deflation sequence are illustrated in FIG. 5.

The proximal, P, and distal, D, balloons are inflated and deflated in a sequence in association with advancement of the different catheter segments 86 and 87. This is carried out so that the catheters can progress in increments under automatic control. Hence, the surgeon or other operator need not direct the catheter continuously by hand, but instead the controller 92 initiates a sequence by which the catheter creeps or advances in increments through a vessel 100 (FIG. 6).

An example of the timing sequence for the advancement of the inner and other catheters 86 and 87 of FIG. 4 or 120 or 130 of FIG. 6 is illustrated in FIG. 5. Once the advancement sequence is initiated, for example, through the input device 96, no further control via the input device is necessary. Instead the controller 92 simply repeats a predetermined sequence to cause incremental movement of the catheter system through the body.

FIG. 5 depicts certain timing actions relating primarily to the inflation and deflation of the balloons, P and D, as well as the forward advancement of the catheters 86 and 87, or 120 and 130.

In step (a), there is an inflation of the proximal balloon P. This causes the catheter 130 to lock against the side wall of the vessel 100 to create an anchor point for the distal end of the catheter 130.

Next, in step (b) the inner catheter 120 is advanced by a certain amount in the vessel 100. Note that, as illustrated in FIG. 6, the distal balloon D is deflated, and thus is not locked in position but is readily moveable in a forward direction with the catheters 110 and 120.

In step (c), the process inflates the distal balloon D, which locks the distal end of catheter 120 to the inner wall of the vessel 100. Subsequently, the proximal balloon P is deflated so that it is no longer locked against the inner wall of the vessel 100. The outer catheter 130 is then free to move.

In step (e) the outer catheter 130 in FIG. 6 is moved forward carrying the proximal balloon P. which has previously been deflated allowing it to move readily through the vessel 100.

After the catheter 130 and its associated proximal balloon P has moved a certain distance, then, as illustrated in step (f) the process again inflates the proximal balloon P, and in step (g) deflates the distal balloon D. Once this occurs, the catheter system is then in the position illustrated in FIG. 6, having advanced by an incremental amount related to the length of movement of the inner and outer catheters 120 and 130.

Note that the particular control illustrated in FIGS. 4-6 does not necessarily require the use of an input device. Alternatively, if an input device is used, it can be of the type that simply initiates a sequence that is stored in the algorithm of controller 92. Hence again, in this way, once the sequence is initiated, then subsequent moves are controlled by the controller 92 and not by any specific manipulations at the input device 96.

Moreover, there may also be provided a force feedback, usually associated with a distal catheter 110. If the distal end of this catheter, or an end effector supported at the distal end, detects an obstruction or some blockage that provides a force feedback signal to the controller, then the controller may interrupt the sequence of steps depicted in the timing diagram of FIG. 5. This enables the surgeon to observe the position of the catheters, for example, through the use of known display techniques including Fluoroscopy, Ultrasound, MRI, CT, or PET.

Figure 7:
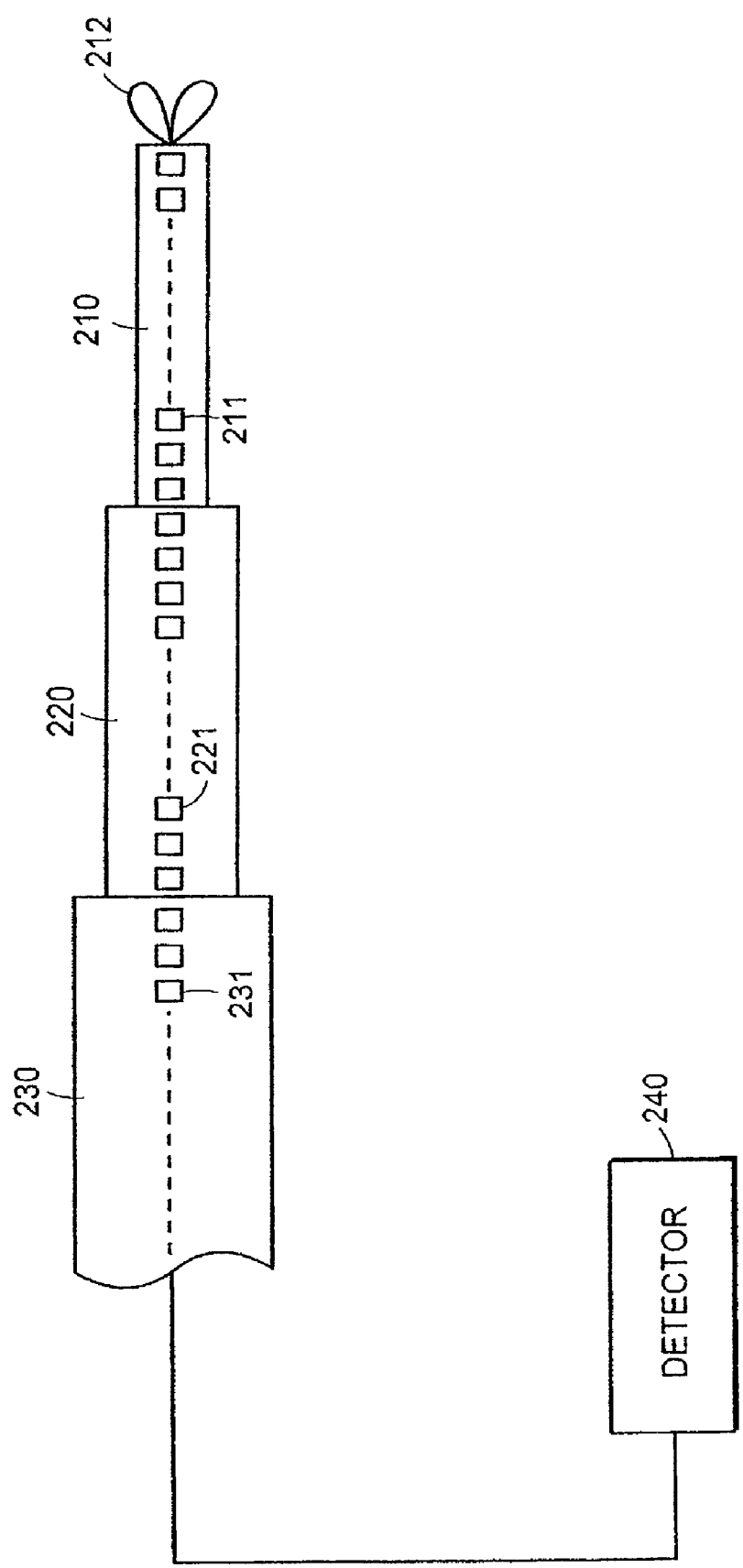
FIG. 7 is a schematic diagram illustrating another aspect of the present invention employing a detector.

Referring now to FIG. 7, there is shown another embodiment of a catheter system having separate catheters 210, 220 and 230, and a detector 240. For illustrative purposes, the catheter 220 may be considered a proximal catheter, while the catheter 210 may be considered a distal catheter. A drive system such as that shown in FIG. 3 is used for the linear translation of the catheters. A particular feature of the catheter system shown in FIG. 7 is a feedback signal provided to the detector 240 to indicate movement of the catheters, as well as relative movement between catheters. To accomplish this, each of the catheters 210, 220, and 230 is provided with indicia 211, 221, and 231, respectively, that may be of the optical type. The detector 240 may be or include a counter that counts passing indicia.

As an example, if the catheter 220 is stationary and the catheter 210 is being moved forward linearly, then the detector 240 such as an optical system can simply read the indicia 211 as the catheter 210 moves coaxially out of the catheter 220. Each of the indicia is separated by a predetermined length and the optical system simply reads each indicia as it moves relative to an adjacent fixed catheter to determine the overall distance of movement of the catheter system.

The detection system 240 illustrated in FIG. 7 may be used with the incremental advancement system depicted in FIGS. 4-6. In connection with the balloons illustrated in FIGS. 4 and 6, mention has been made of the incremental forward movement of the inner and outer catheters 86 and 87, or 120 and 130. The optical detection scheme illustrated in FIG. 7 can be used to measure the distance of movement of either or both of the catheters.

Figure 8:
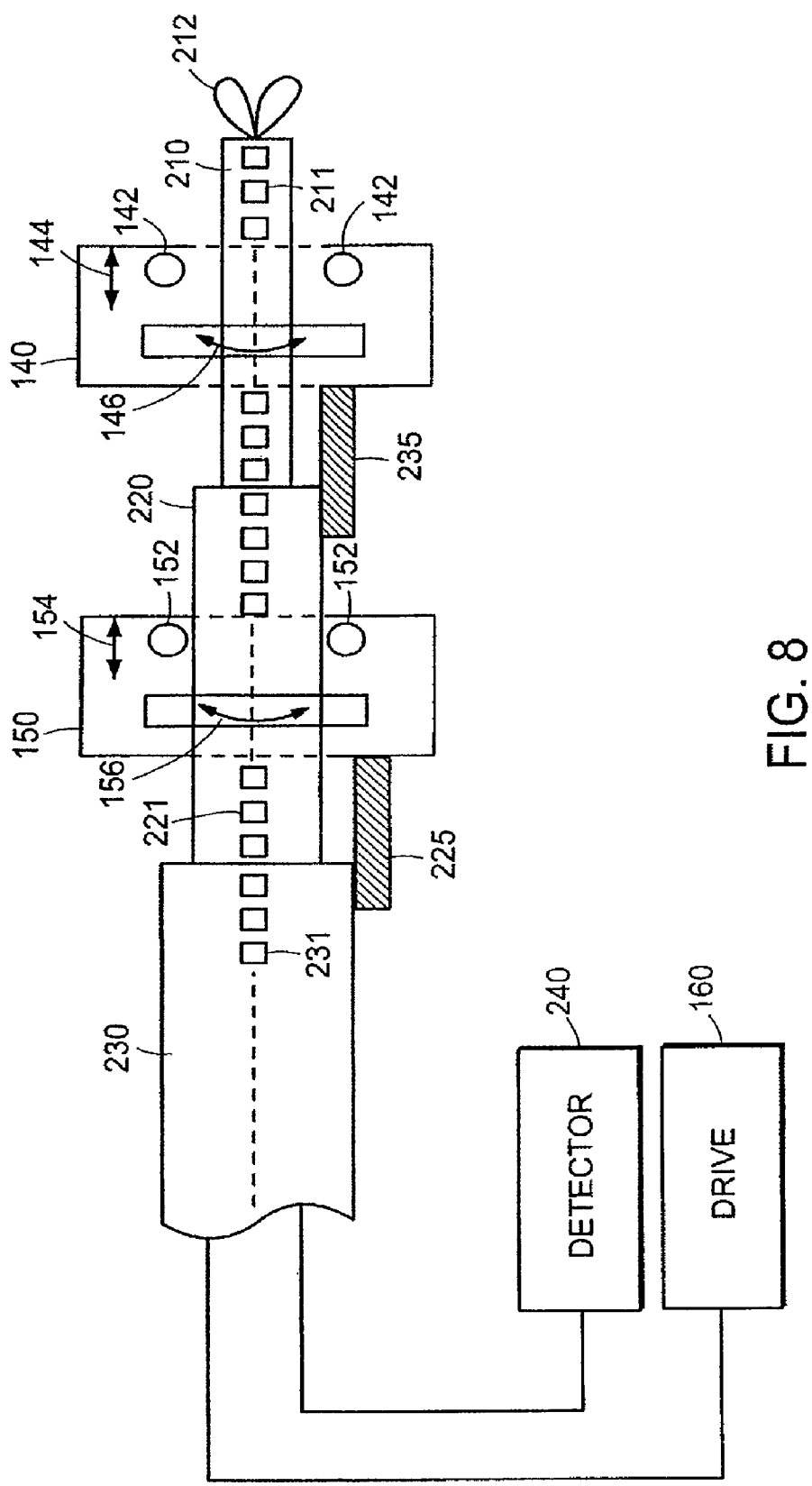
FIG. 8 is a schematic and block diagram of still another embodiment of the present invention.

A further embodiment is illustrated in the schematic and block diagram of FIG. 8. Unlike the drive arrangement shown in FIG. 3 where coaxial catheters are driven from their proximal ends, the catheters 210, 220, and 230 shown in FIG. 8 are driven from their distal ends. The catheter system also implements the indicia and detector 240 described with reference to FIG. 7.

Here, the catheter 220 is considered the proximal catheter and the catheter 210 is considered the distal catheter. The operation of the catheters 210, 220, and 230 are controlled from the drive member 160. The drive member 160 may be placed at the master station of FIG. 3, or controlled from a remote location such as at the master station, usually with surgeon input control.

Each catheter is driven relative to an adjacent coaxial catheter member, such as catheter 220 relative to catheter 230, with drive mechanisms 150 and 140 mounted to frame pieces 225 and 235 extending from more proximal catheters.

In FIG. 8 there are illustrated two drive blocks 140 and 150 which control the respective catheters 210 and 220. Note that the catheter system of FIG. 8 may also include the proximal drive arrangement of FIG. 3 for one or more of the catheters. If both proximal and distal drive is used for any one particular catheter, then the proximal drive may be considered as a "coarse" drive while the more distal drive may be considered as a "fine" drive.

The drive block 140 includes wheels 142 for controlling linear translation of the catheter 210, as illustrated by arrow 144. In the drive block 140 there is also illustrated rotational translation of the catheter 210, as illustrated by the arrow 146. In a similar manner, the linear translation relating to drive block 150 is represented by wheels 152 indicated by the arrow 154. Also, with regard to drive block 150, and catheter 220, the arrow 156 illustrates rotational movement of the catheter 220 produced by the drive block 150.

FIG. 8 also illustrates the feedback signal to the detector 240 to sense incremental of movement of the respective catheters. For this purpose, on each of the catheters there is provided indicia that may be of the optical type described earlier. In FIG. 8 these are indicated as indicia 211 on catheter 210, indicia 221 on catheter 220, and indicia 231 on catheter 230. The detector 240 may include a counter that counts passing indicia to indicate the liner distance of relative movement between catheters.

Figure 10:
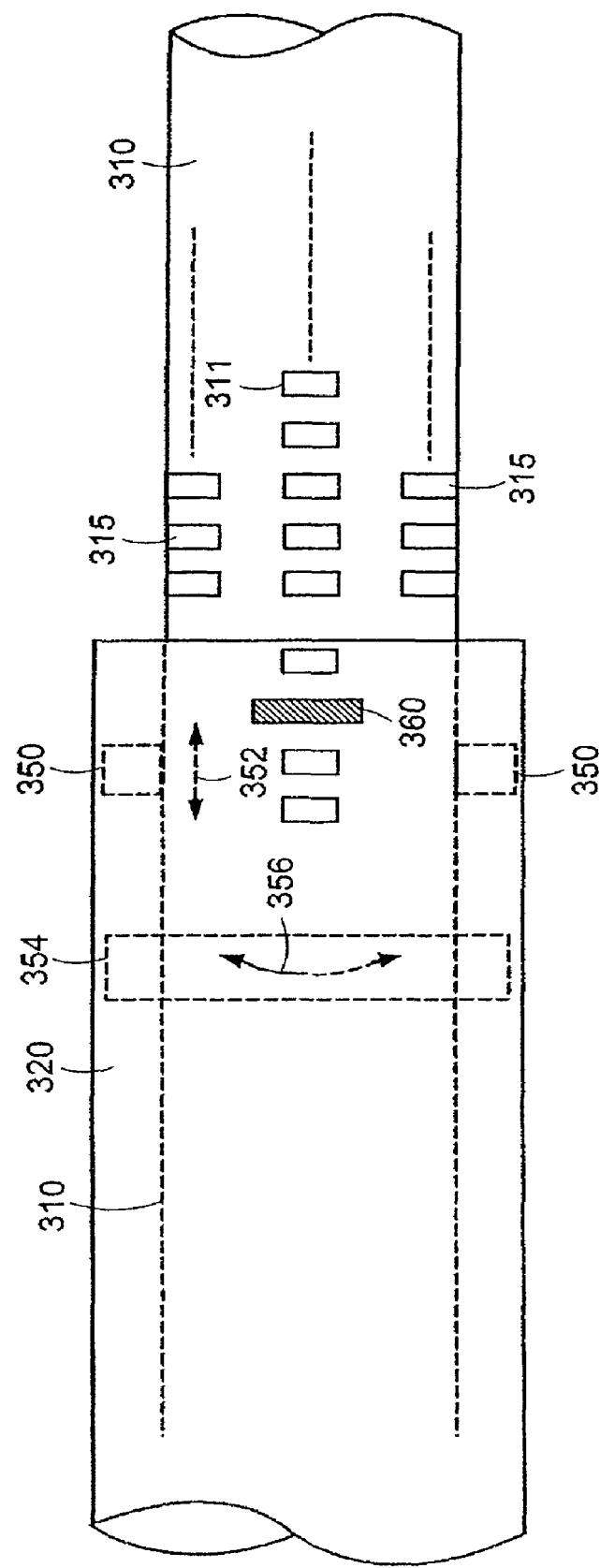
FIG. 10 illustrates another embodiment of the invention for distal drive of one of the catheters.

Although the drive blocks 140 and 150 are shown in a schematic fashion about each of their respective catheters, it is understood that the drive mechanisms can also be employed within the catheter construction, such as shown in FIG. 10, or other drives may be employed between adjacent catheters. Also, the block 160 illustrated in FIG. 8 as a drive block may in practice be cabling that connects back through the catheters to the motor array, such as the motor array 70 depicted in FIG. 3. In this way, at an input device, such as the input device 76 in FIG. 3, the surgeon can control the movement of the catheters in both a proximal manner and in a distal manner, or either manner.

The feedback at detector 240 may be incorporated with the drive 160 so that the drive provides for "fine' movement of catheters in an incremental manner. The movement is fed back by way of detector 240 to provide for fine adjustment of the catheters, particularly the smaller diameter distal catheter 210.

Mention has been made that control of the movement of the catheters can be provided at both the proximal and distal ends of the coaxial catheter system. For certain procedures, it may be advantageous to control the proximal end of the catheters, as well as directly control the movement at the distal end of the catheters. For example, FIG. 9 depicts a coaxial catheter system extending through the aorta 300 of the heart 304 and used in a vascular artery 302 that may be considered as including a main artery and several branches of the artery that are to be negotiated by the catheter system.

Figure 9:
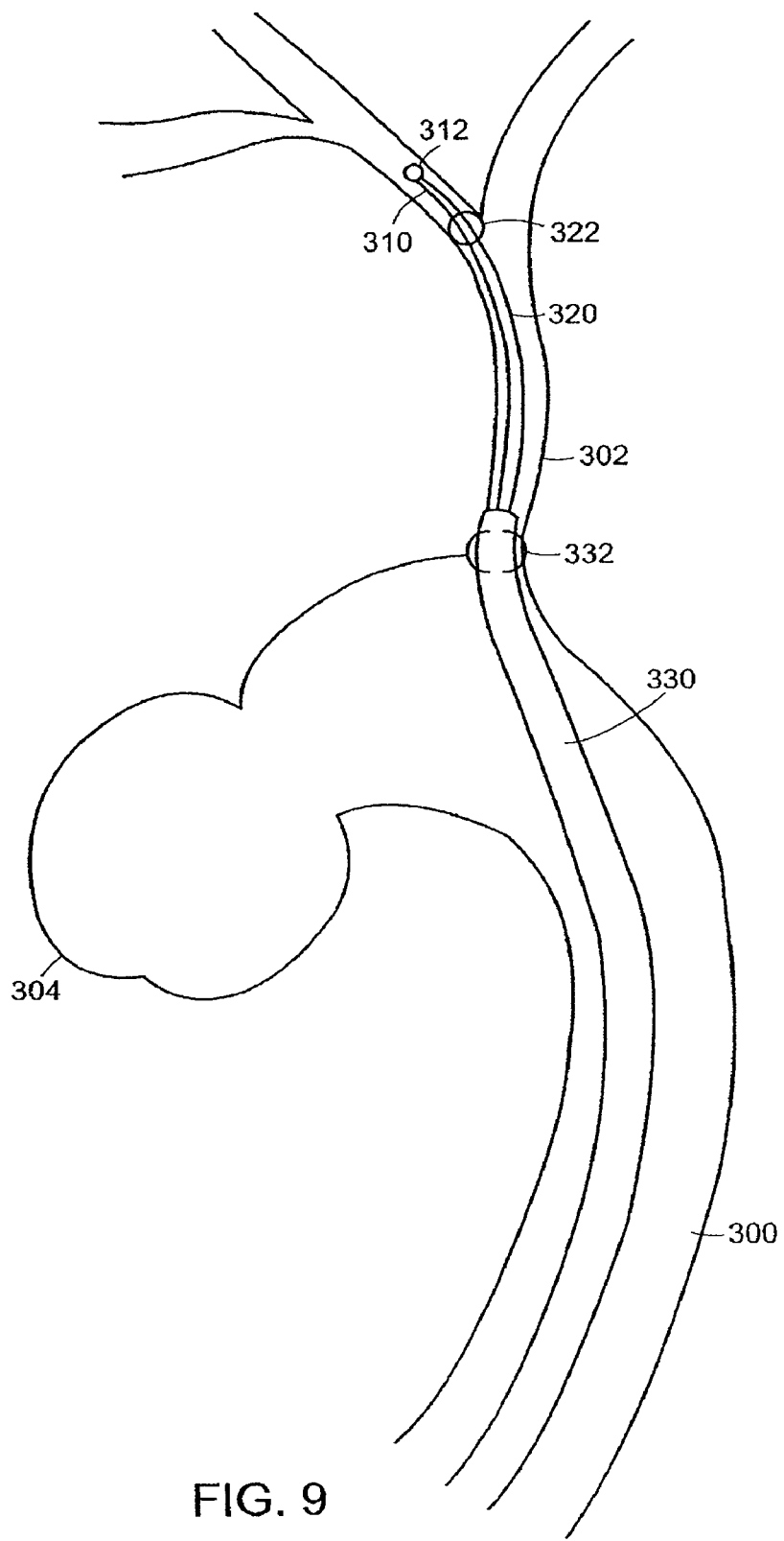
FIG. 9 illustrates another principle of the present invention in a coaxial catheter system illustrated being used in a vein or artery.

In the particular embodiment illustrated in FIG. 9 the coaxial catheter system includes a large outer catheter 330, a middle catheter 320, and a small distal or inner catheter 310. The distal end of the catheter 310 supports or carries an end effector 312 which may be in the form of a jaw member. For the particular system depicted in FIG. 9, the outer catheter 330 and the middle catheter 320 are driven from their respective proximal ends in a manner as illustrated in FIG. 3 with the use of the input device 76, controller 72, and motor array 70.

Figure 9A:
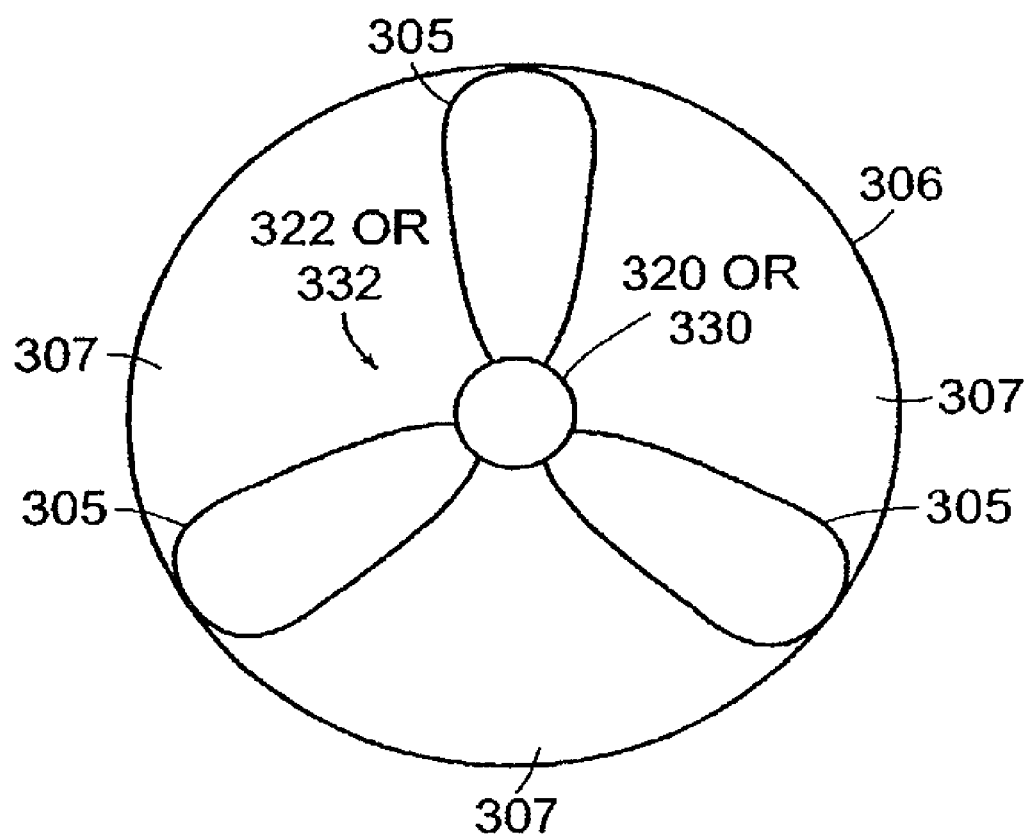
FIG. 9A illustrates a multi-lobed balloon of the system of FIG. 9.

To position each of the separate catheters, there is illustrated in FIG. 9 a fixing or securing means such as balloon 332 located at the distal end of large outer catheter 330 and balloon 322 located at the distal end of the middle catheter 320. Each of these balloons may be inflated to hold its corresponding catheter in a relatively fixed position in the body vessel. Alternatively, rather than the use of balloons, other securing devices may be employed such as sonic type of expandable mechanical member. Regardless of the type of securing member employed, it is capable of being operated by the surgeon from a remote location at the master station, and at the appropriate time selected by the surgeon. The balloons 322 and 332 can be a single lobed balloon that totally obstructs the vessel when inflated. Alternatively, the balloons may have a multi-lobed configuration as illustrated in FIG. 9A. The balloon 322 or 332 shown in FIG. 9A has three lobes 305 that when inflated in a vessel 306 allows fluid to flow in the space 307 between the lobes. The balloon 322 or 332 can have fewer or more than three lobes in other arrangements. In certain implementations, the individual lobes can be inflated independently of each other.

Initially, both the middle catheter 320 and the small inner catheter 310 may be in a withdrawn position, coaxially positioned within the outer catheter 330. When the outer catheter 330 is controlled by the surgeon to be positioned in the manner illustrated in FIG. 9, the surgeon can then instruct the balloon 332 to inflate to secure the outer catheter 330 in the position illustrated in FIG. 9. The balloon 332 expands against the walls of the vessel and essentially locks the outer catheter in position, particularly at its distal end.

Next, under the control of the surgeon through the use of an input device, the middle catheter 320 is moved forward linearly through the vessel of the anatomy. The control of the forward movement of the catheter 320 relative to the catheter 330 may be carried out in a manner illustrated in FIG. 3 from the proximal end of the catheter 320.

Previously, mention was made that the balloon 332 is inflated to secure the outer catheter 330. After the middle catheter 320 is moved forward some distance, then the balloon 322 may also be inflated. This procedure is under the surgeon's control at the master station through the input device to now secure the distal end of the middle catheter 320 at an appropriate position within a body vessel.

For "fine" control of the small inner catheter 310, it is intended, in the embodiment of FIG. 9, that the control of the inner catheter 310 is implemented in the manner illustrated in FIG. 8 in which the support and drive block 140 can provide direct drive of the inner catheter's 310 forward linear movement out of the middle catheter 320. Although the drive is located at the distal end of the catheter, the drive is remotely controlled by the surgeon at the master station. Again, this control can be by way of an input device such as an input interface or a joystick moved in a direction to cause a consequent movement of the various catheters depicted in FIG. 9.

Because of the significant length of the catheters that may be employed in a surgical procedure, it may be desirable to provide direct drive of the inner catheter 310 at its distal end, rather than drive it at its proximal end. For example, this may be particularly desirable when the length of the entire catheter system is so long that it may have some tendency to deflect or bend even when secured by, for example, the balloons 322 and 332.

After the balloons 322 and 332 are inflated, the surgeon at the master station can continue to control the forward movement of the distal end of inner catheter 310. As indicated previously, the drive for the inner catheter 310 is typically of the type illustrated in FIG. 8, or in FIG. 10 discussed below.

In FIG. 10, the small diameter inner catheter 310 is driven relative to the middle diameter catheter 320. The linear movement of the catheter 310 is illustrated by the arrow 352 when driven by the wheels 350. The rotation of the catheter 310 relative to the catheter 320 is driven the block 354, as indicated by the rotational arrow 356.

FIG. 10 also illustrates a detector or reader 360. This again may be an optical device that detects the passage of the indicia 311 on the inner catheter 310. Appropriate electrical signal lines coupled from the detector 360 back to the master station transmit information related to the movement of the inner catheter 310 relative to the middle catheter 320.

The detector 360 may also be used for detecting rotation of the catheter 310 relative to the catheter 320. For this purpose, in addition to the linear set of indicia 311 on the catheter 310, the catheter 310 is also provided with additional indicia 315 that extend about the circumference of the catheter. The reader 360 is able to read not only linear passage of indicia 311, but also read rotation of the indicia 315 from one linear set of indicia 311 to the next.

Although a single detector 360 is shown in FIG. 10, other detectors may also be employed. For example, one detector could be used for detecting linear translation of the catheter 310, and a second detector could be used for detecting rotation of the catheter 310 with the use of indicia 315.

Figure 11A:
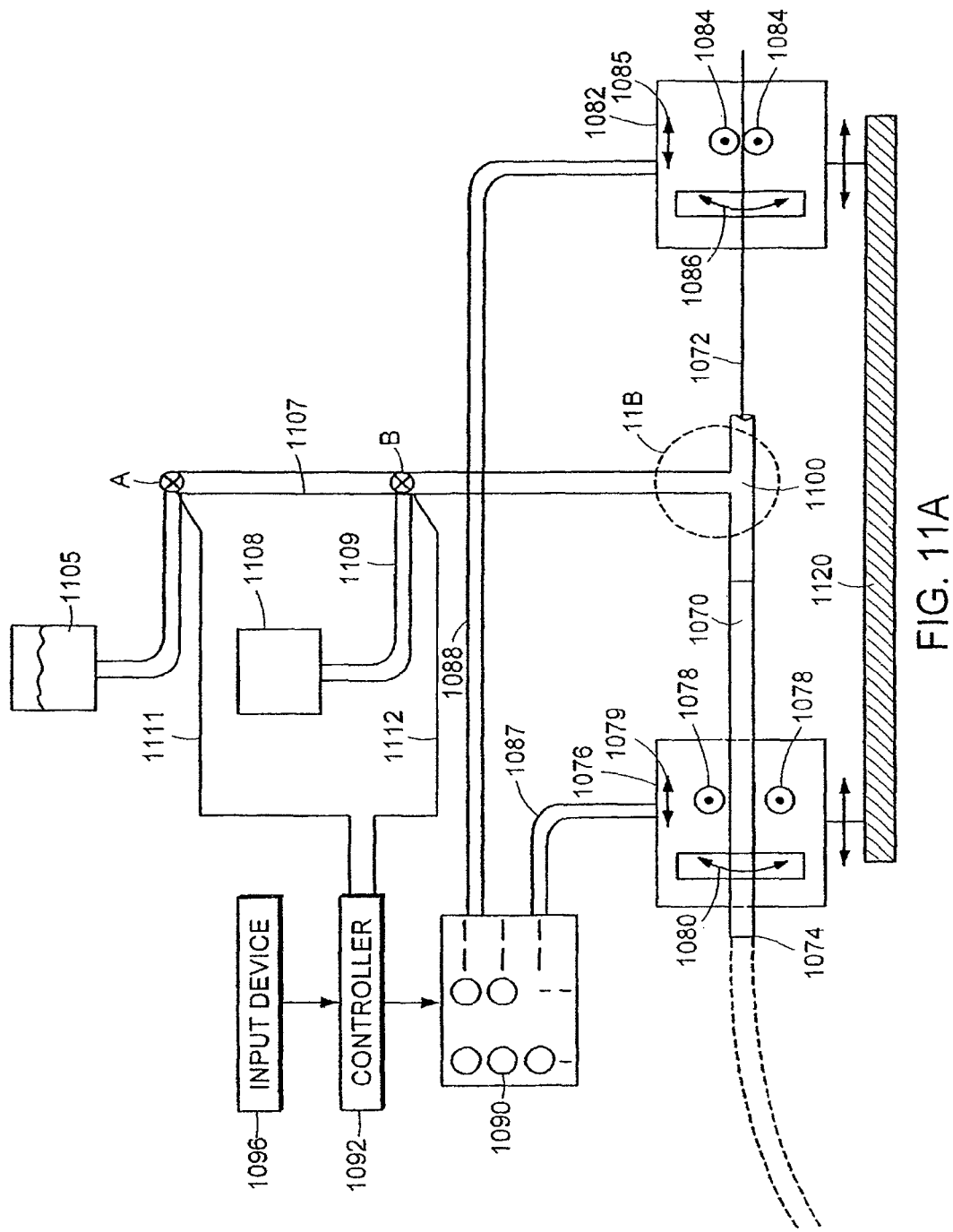
FIG. 11A a block and schematic view a catheter drive system with a fluid delivery system in accordance with the invention.

The catheter drive system described above can be implemented in other configurations as well. For example, there is shown in FIG. 11A a catheter drive system associated with a fluid or drug delivery system. Note in FIG. 11A, emphasis is placed on the proximal end of a catheter 1070 and guide wire 1072. The more distal portion of the catheter is identified by the dotted lines. Details of the distal portions of the catheter 1070 and guide wire 1072 can be found in the U.S. application entitled "Catheter Drive System," by Weitzner, U.S. application Ser. No. 10/216,067, filed herewith, the entire contents of which are incorporated herein by reference.

At some position along the catheter 1070, there is a patient interface illustrated at 1074 where the catheter may be considered as entering into the patient's body. The entry of the catheter may, for example, be percutaneously, via an incision, or even through a natural body orifice.

A support block 1076 supports the catheter 1070 in a manner to enable at least two degrees-of-freedom of the catheter including axial movement of the catheter to an anatomic body target sit; as well as rotation of the catheter. The support block 1076 controls both the linear translation of the catheter 1070 by the wheels 1078, as indicated by the arrow 1079, and the rotational translation of the catheter, as illustrated by the arrow 1080. Again, further details of such a catheter support system illustrating multiple degrees-of-freedom can be found in the U.S. patent application Ser. Nos. 10/023,024, 10/011,371, 10/011,449, 10/010,150, 10/022,038, and 10/012,586 mentioned earlier.

In FIG. 11A, there is also a block 1082 which controls the movement of the guide wire 1072. In particular, the wheels 1084 move the guide wire 1072 in a linear manner in the direction 1085. The block 1082 is also able to rotate the guide wire 1072 in the direction 1086. Note that the blocks 1076 and 1082 can be supported on a common support structure 1120. Although the support 1120 provides a physical connection between the blocks 1076 and 1082, the blocks are operated independently so that the guide wire 1072 and the catheter 1070 can be driven independently of each other.

The drive or support blocks 1076 and 1082 are coupled to an electromechanical drive member or motor array 1090 that controls the movements of both the catheter 1070 and the guide wire 1072 with at least two degrees-of-freedom. In particular, mechanical cablings 1087 and 1088 couples the motor array 1090 to the support blocks 1076 and 1082, respectively. The motor array 1090 is also coupled to a controller 1092 that directs a plurality of motors in the motor array. An input device 1096 provides an interface to the system for use by a surgeon.

The mechanical cablings 1087 and 1088 transmit the mechanical movements of the various motors in the motor array 1090 to the respective support blocks 1076 and 1082 to provide the linear and rotational movements of the catheter 1070 and guide wire 1072. Thus, in the motor array 1090, there may be at least one motor for the linear translation and a separate motor for the rotational translation for the block 1076. Similarly, there can be motors in the motor array 1090 for both the linear and rotational translations of the support block 1082.

The controller 1092, may be a microprocessor that receives input commands from the input device 1096. The input device 1096 may include various types of controls such as a dial, joystick, wheel or mouse. A touch screen may also be employed as the input device 1096 to input information about the desired location of a particular portion of the catheter. Details of such a tracking system can be found in the U.S. application entitled "Catheter Tracking System," U.S. application Ser. No. 10/216,669, mentioned earlier. Such a tracking system enables an operator, such as a surgeon, through the input device to select a particular anatomic body site and direct the catheter directly and automatically to that site.

Although a manifold 1100 is shown with a single port, the manifold may include multiple ports. The manifold 1100 provides a delivery conduit to the catheter 1080 for the delivery of fluids to a site in the patient's body. For example, one of the fluids 1105 employed may be a contrast fluid for purposes of visualization, which is coupled to a feed line 1107 by a valve A. There may also be a drug delivery system indicated generally at 1108 coupled to the feed line 1107 by way of a line 1109 to a valve B. Alternatively, the manifold 1100 can be provided with two separate ports with a respective valve A and B in each of these ports.

Figure 11B:
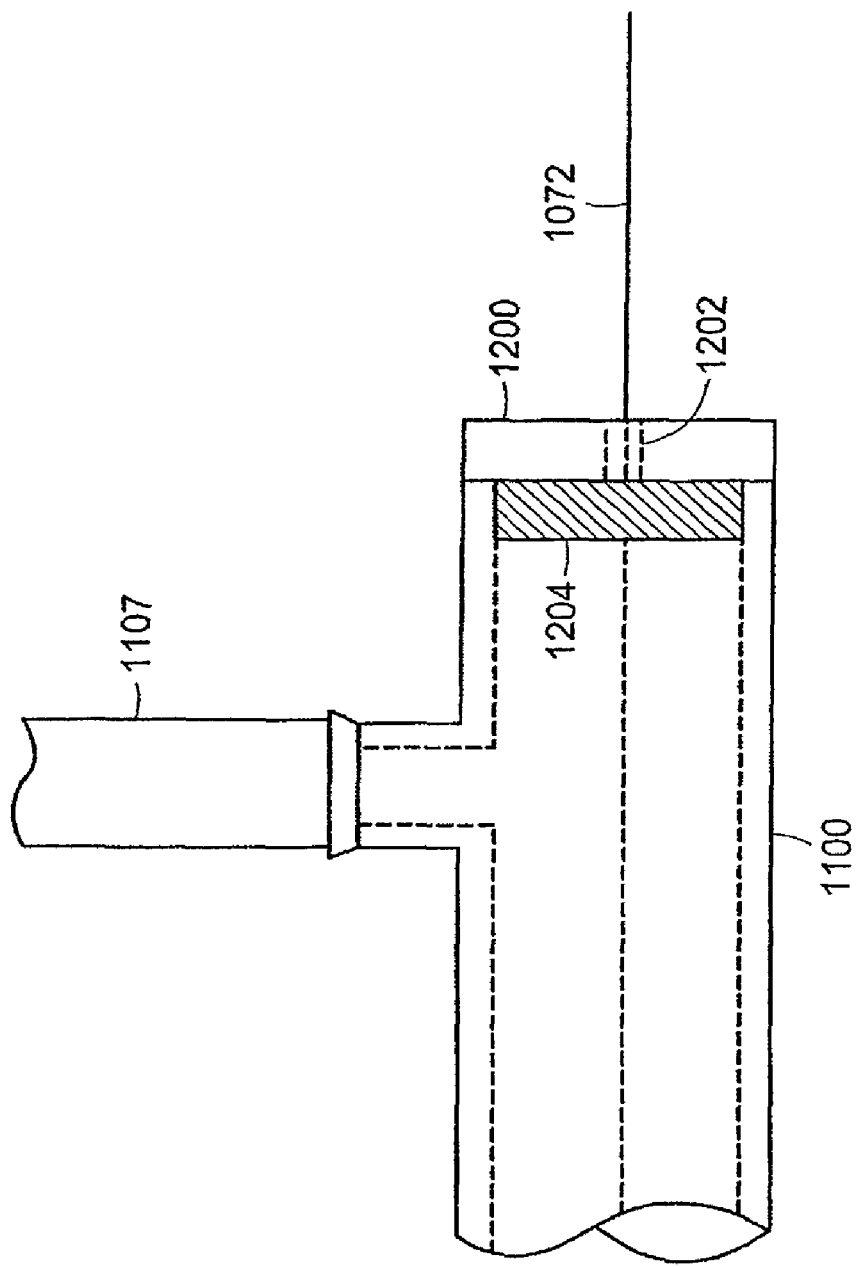
FIG. 11B is a close-up view of a manifold of the fluid delivery system of FIG. 11A.

As shown in FIG. 11B, the manifold 1100 includes an end piece 1200 sealed to the back end of the manifold 1100 and provided with an opening 1202 through which the guide wire 1072 enters into the manifold 1100, and hence the catheter 1070. Positioned within the manifold 1110 and adjacent to the end piece 1200 is a gasket 1204. The guide wire 1072 pierces the gasket 1204 such that the gasket forms a seal about the guide wire. Thus, as fluid enters from the feedline 1107 into the manifold 1100, the gasket 1204 prevents the fluid from leaking out the back end of the manifold 1100.

As indicated previously, the input device 1096 may take on a variety of different forms. If a wheel, dial, or pivoting switch is employed as the input device 1096, then one of these may be used for controlling the two degrees-of-freedom of movement of the catheter 1070, while another such device is used to control the two degrees-of-freedom of movement of the guide wire 1072. Thus, the operator has independent control of the drive or support blocks 1076 and 1082 byway of the input device 1096. This permits the operator to selectively move the guide wire 1072 and the catheter 1070 independently of each other. Typically, the operator advances the guide wire 1072 a certain distance, and then the catheter 1070, such that the guide wire 1072 can be used to access certain twists or turns in a body lumen such as an artery or vein.

The input device 1096 may also operate means such as buttons, switches, etc. that provide signals through lines 1111 and 1112 to the respective valves A and B for controlling the dispensing of liquids from the fluid sources 1105 and 1108. Although shown coupled to the controller 1092, the lines 1111 and 1112 can be coupled directly to the input device 1096 in other implementations.

When the system is in operation, the surgeon advances the catheter 1070 and guide wire 1072 through the patient's body with the drive system. To provide visualization of the end of the catheter, the surgeon can instruct, with the input device 1096, the valve A to open. That is, the surgeon interfaces with the system through the input device 1096 to generate a signal on line 1111 that opens the valve A to dispense a contrast fluid through the manifold 1000 and the catheter 1070 to the target site of interest. Similarly, the surgeon may deliver drugs to the target site by instructing the valve B to open which would allow drugs from the source 1108 to flow through the catheter 1070 into the body.

In the following discussion, greater detail will be provided about the drive mechanisms (FIGS. 12-16) and various devices (FIGS. 17-19) used to couple the medical instruments to the drive mechanisms. Although the drive mechanisms and connectors are described in reference to the catheter 1070 and guide wire 1072 discussed above, they can be used in any number of combinations with any of the other medical instruments described earlier.

The catheter 1070 referred to in these figures is of the type commonly used in angioplasty. The catheter 1070 includes a first leg 1300 joined with a second leg 1302 at a coupler 1304, and a single extended leg 1306 that extends from the coupler 1304. Typically, a part or much of the extended leg 1306 is the portion of the catheter 1070 that is inserted into the patient. The leg 1302 is connected to an end piece 1305 through which the guide wire 1072 is inserted such that the guide wire 1072 typically extends from outside the end piece 1305 through the legs 1302 and 1306. As are the legs 1302 and 1306, the leg 1300 is hollow to allow the transmission of a liquid or gas through the leg 1306 to the surgical site. Hence, the leg 1300 would function in much the same way as the feedline 1107 shown in FIG. 11. The leg 1300 is also provided with a valve 1307 that controls the delivery rate of the liquid or gas, and prevents the liquid or gas from escaping once the liquid or gas source is disconnected from the leg 1300. Note that a gasket is typically located in the coupler 1304 or the end piece 1305 that forms a seal with the guide wire 1072 to prevent the liquid or gas from escaping out the opening of the end piece 1305.

Referring now to FIGS. 12 and 12A, the drive or support block described earlier is identified as drive mechanism 1308a associated with the catheter 1070. As can be seen in FIG. 12A, which is a view of the drive mechanism along the length of the leg 1306, the drive mechanism 1308 includes a gripping device 1310 in which the catheter 1070 is secured, and a motor 1312. A belt 1314 is wrapped around pulleys 1315a and 1315b of the motor 1312 and gripping device 1310, respectively. Hence, as the motor 1312 rotates, this rotary motion is transmitted to the gripping device 1310 through the belt 1314 as indicated by the double arrow 1316, such that the catheter 1070 rotates accordingly as indicated by the double arrow 1318 (FIG. 12).

Figure 13:
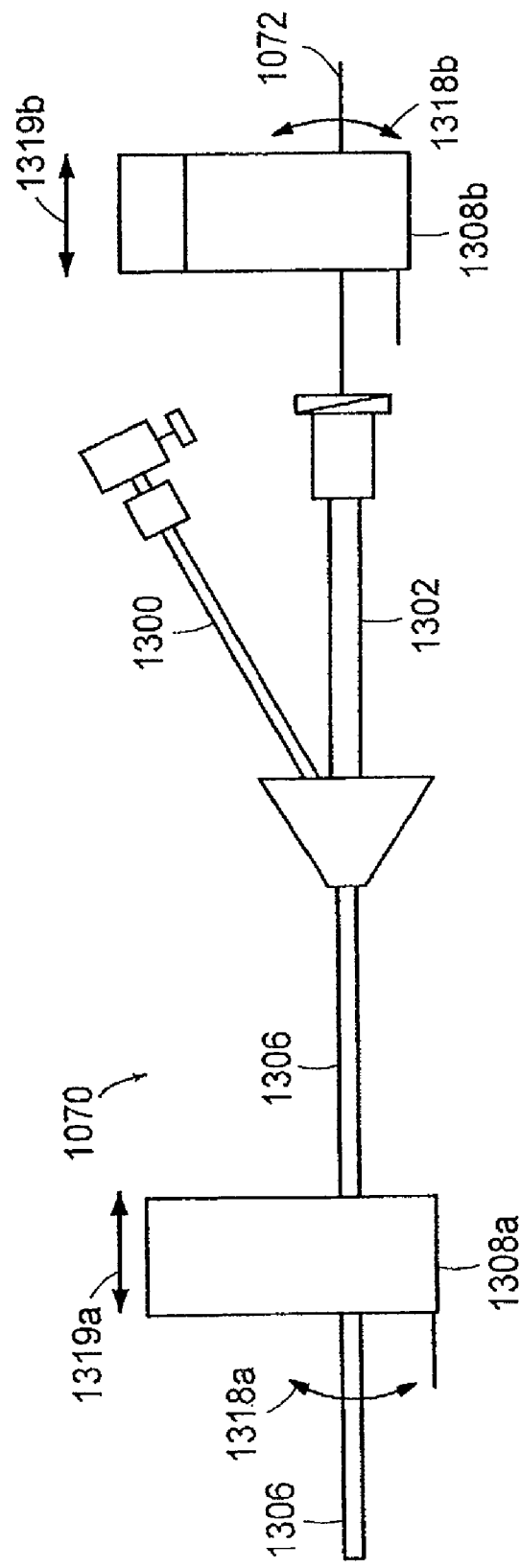
FIG. 13 illustrates the catheter of FIG. 12 and a guide wire coupled to respective drive mechanisms in accordance with the invention.
Figure 14:
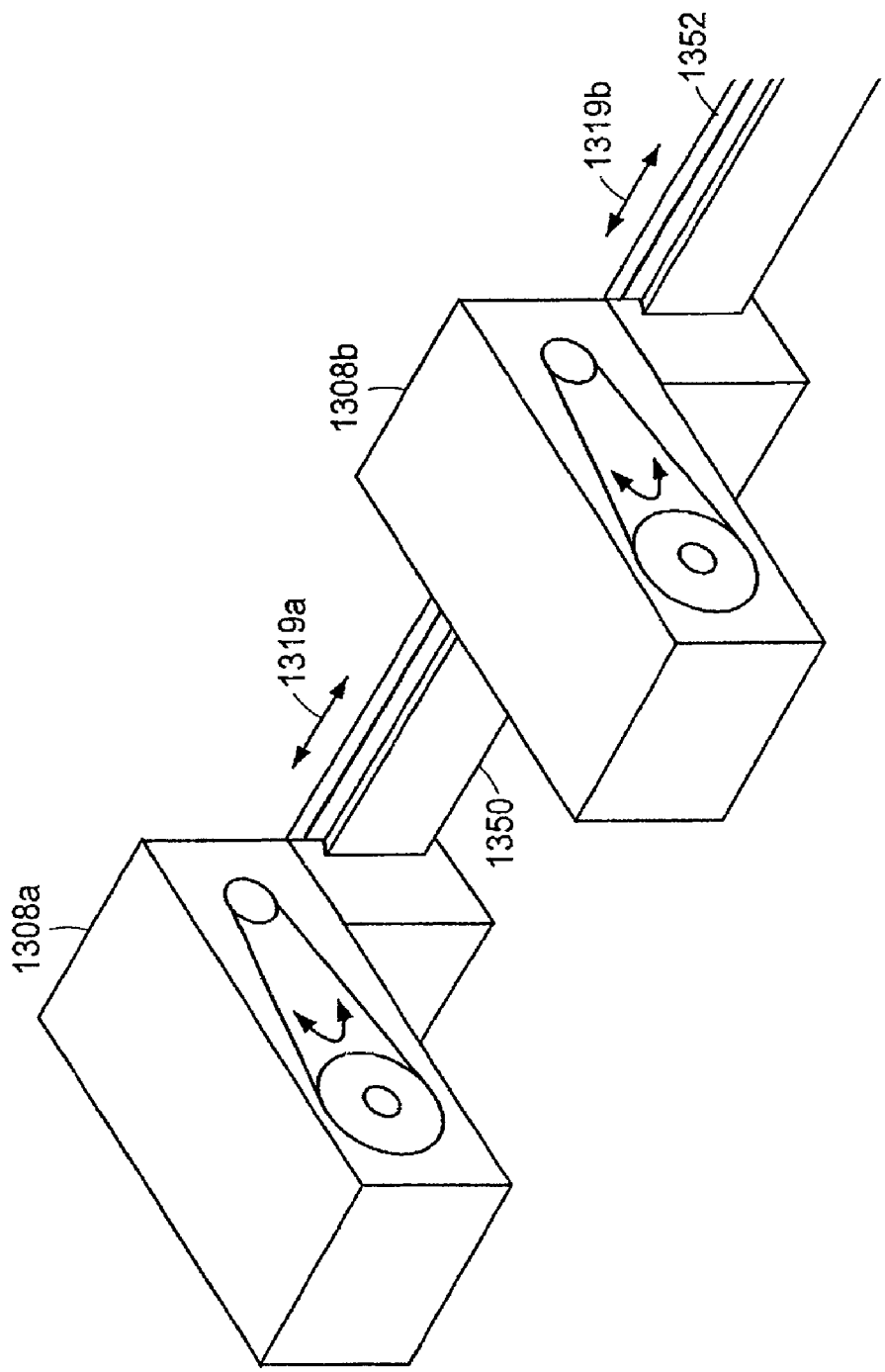
FIG. 14 illustrates the linear movement of the drive mechanisms of FIG. 13.

As shown in FIG. 13, a similar type of drive mechanism 1308b can be coupled to guide wire 1072 to provide it with a rotary motion as indicated by the double arrow 1318b. In addition, the drive mechanisms 1308a and 1308b shown in FIG. 13 also provide the catheter 1070 and guide wire 1072 with linear motion as indicated by the double arrows 1319a and 1319b (referred to generally as direction 1319), respectively. In certain embodiments, as shown in FIG. 14, the drive mechanisms 1308a and 1308b are supported on and slide back and forth along respective rails 1350 and 1352.

To move the drive mechanisms 1308a and 1308b (referred to generally as drive mechanism 1308) linearly in the direction 1319, various configurations can be used as illustrated in FIGS. 15A, 15B, and 15C. Referring in particular to FIG. 15A, there is shown a lead screw drive arrangement 1360 with a threaded connector 1362 attached to the drive mechanism 1308. A lead screw 1364 is threaded through the connector 1362 and coupled to a stationary motor 1366. Accordingly, rotary motion of the lead screw 1364 induced by the motor 1366 in the direction 1368 results in a linear motion of the connector 1362. Since the connector 1362 is attached to the drive mechanism 1308, linear motion of the connector 1362 produces a consequent linear motion of the drive mechanism 1308 in the direction 1319.

Referring now to FIG. 15B, there is shown a rack and pinion drive arrangement 1370 for moving the drive mechanism 1308 in a linear manner. The rack and pinion drive 1370 includes a rack 1372 attached to the drive mechanism 1308, and a pinion 1374 coupled to a stationary motor 1376. The teeth of the pinion 1374 engage with those of the rack 1372 such that as the motor 1376 rotates the pinion 1374 in the direction 1378, the rack 1372 and hence the drive mechanism 1308 moves linearly back and forth in the direction 1379.

Turning now to FIG. 15C, there is illustrated yet another configuration for moving the drive mechanism 1308 linearly. In particular there is shown a belt/pulley drive 1380 that includes a belt, chain or cable 1382 wrapped around a pulley 1386 and a motor pulley 1384 coupled to a stationary motor. The belt, chain, or cable 1382 is attached in turn to the drive mechanism 1308 with a connector 1388. Hence, rotary motion of the motor pulley 1384 produced by the motor is transformed into a linear motion of the connector 1388. Thus, as the motor rotates the motor pulley 1384, the drive mechanism 1308 moves back and forth in the direction 1319.

Figure 16:
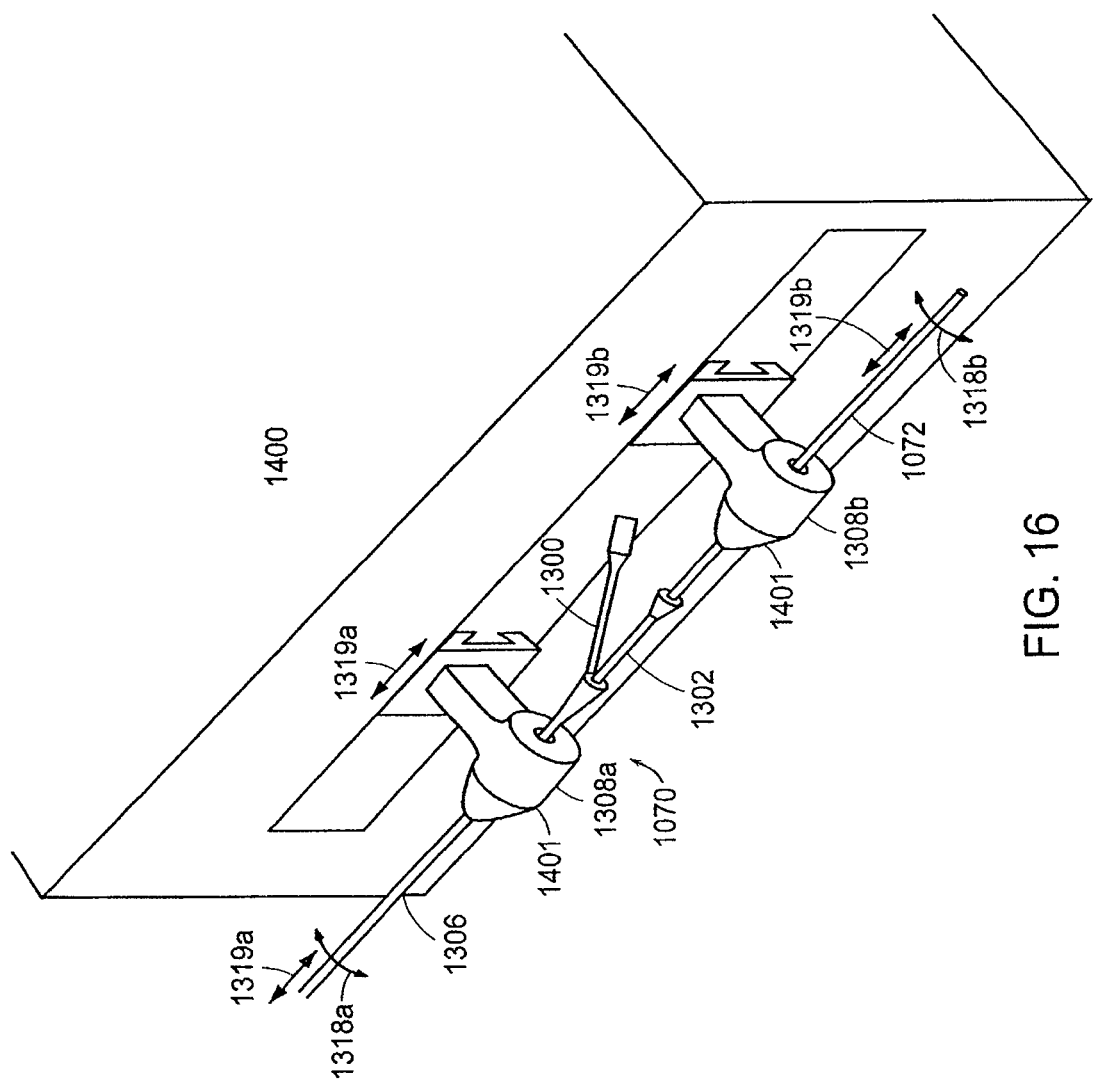
FIG. 16 is a perspective view of the catheter and guide wire of FIG. 13 shown coupled to respective drive mechanisms of a base unit.
Figure 16A:
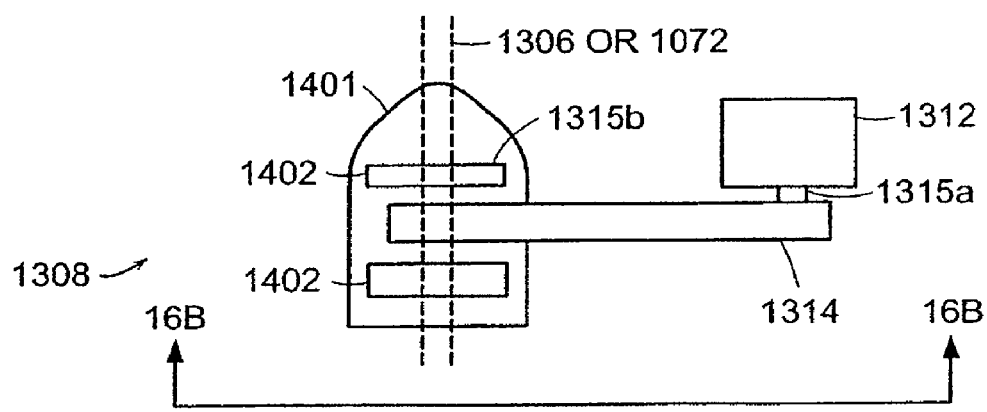
FIG. 16A is a top view of one of the drive mechanisms shown in FIG. 16.
Figure 16B:
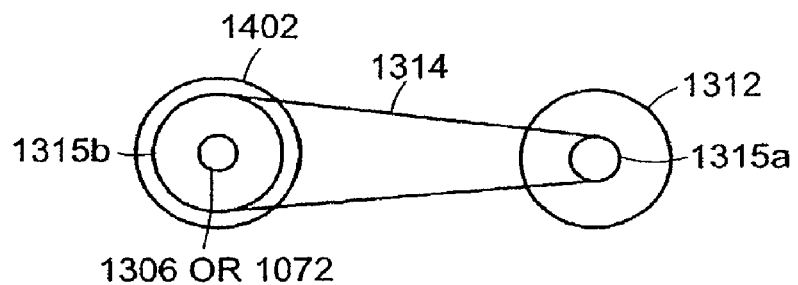
FIG. 16B is a view of the drive mechanism of FIG. 16A taken along the line 16B-16B.

Greater detail of the catheter 1070 and guide wire 1072 arrangement of FIG. 13 is illustrated in FIG. 16, and that of the drive mechanism 1308 is shown in FIGS. 16A and 16B. In particular, the catheter 1070 and guide wire 1072 are shown as a typical "off-the-shelf" apparatus coupled to a base unit 1400. That is, the base unit 1400 is meant to be easily coupled to and decoupled from any number of medical instruments, such as the catheter 1070 and guide wire 1072 combination. In other implementations, such as some of those described earlier, the medical instrument and base unit is considered as a single instrument not to be decoupled from each other.

Referring now in particular to FIGS. 16A and 16B, in addition to the features illustrated in FIG. 12A, the drive mechanism 1308 includes a housing 1401 which encloses much of the moving parts of the drive mechanism 1308. As described before, rotary motion of the motor 1312 is transferred by the belt 1314 to the guide wire 1072 or the leg 1306 of the catheter 1070 via the pulley 1315b coupled to the gripping device 1310 (FIG. 12A). The pulley 1315b itself is supported in the housing 1401 with a pair of bearings 1402.

Figure 17A:
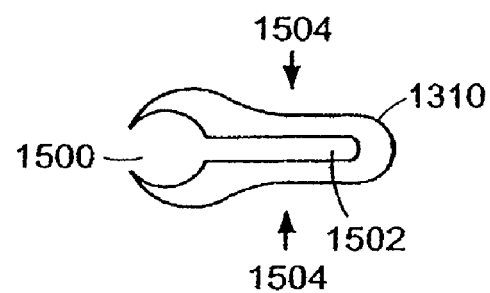
FIGS. 17A-17C illustrate a connector used to couple the catheter and guide wire to their respective drive mechanisms.
Figure 17B:
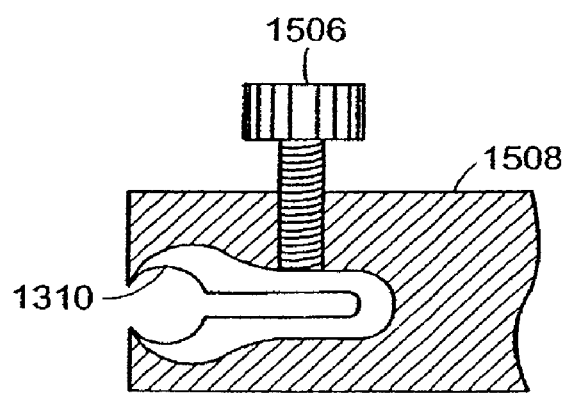
Figure 17C:
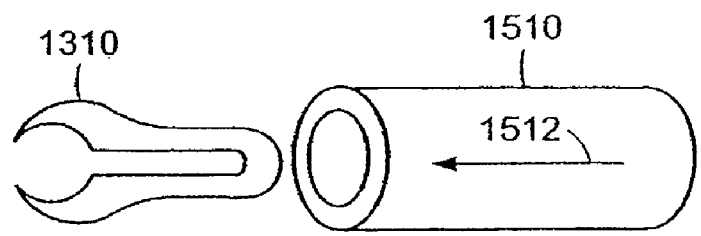
Figure 18:
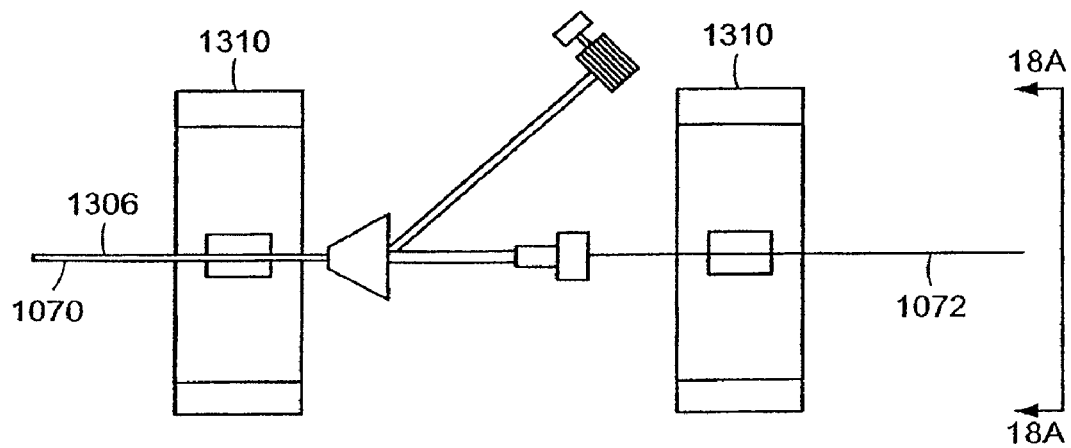
FIGS. 18 and 18A illustrate an alternative embodiment of the connector.

Turning now to the discussion of the connector 1310, to facilitate coupling the catheter 1070 and the guide wire 1072 to their respective drive mechanisms 1308, many types of connectors can be used. In some implementations, a Toohy Borst type of fitting may be optimal. Another type of connector 1310 is shown in FIG. 17A, in which the leg 1306 or guide wire 1072 would be placed in an enlarged portion 1500 of a slot 1502. A clamping force 1504 would then be provided to secure the leg 1306 or guide wire 1072 to the drive mechanism. For example, as shown in FIG. 17B, the clamping force could be provided with a thumb screw 1506 threaded into a block 1508 in which the connector 1310 is mounted. In another type of arrangement shown in FIG. 17C, a sliding ring 1510 is fitted over the connector 1310 in the direction 1512. The clamping force can also be provided by a vise like device that functions similar to a collet/pin vise.

Figure 18A:
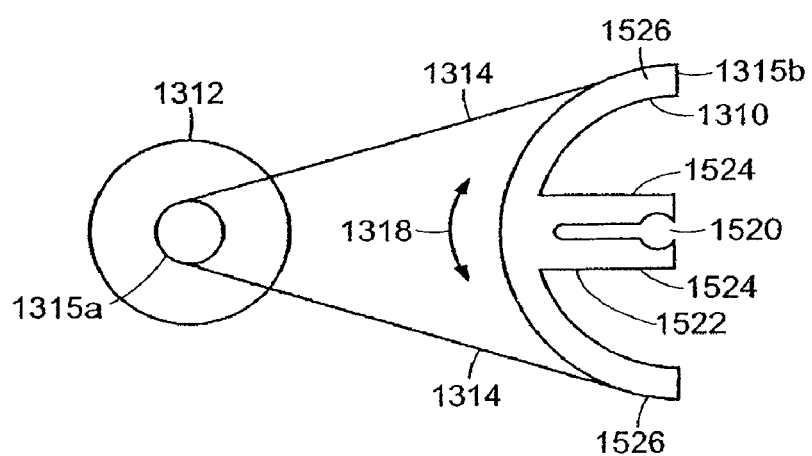

In another embodiment, as shown in FIG. 18A, the connector 1310 and the pulley 1315b are one and the same device. Here, the leg 1306 or guide wire 1072 snaps into an enlarged portion 1520 of a slot provided in an extended segment 1522 of the connector device 1310. Since, the enlarged portion 1520 is slightly smaller than the diameter of the leg 1306 or the guide wire 1072, the legs 1524 of the segment 1522 provide a sufficient clamping force to the leg 1307 or guide wire 1072. In this arrangement, the belt 1314 is wrapped around the pulley 1315a of the motor 1312 and attaches to the two curved segments 1526 of the connector 1310. Thus, rotary motion of the pulley 1315a produces a rotary motion of the connector 1310, and hence the leg 1306 or guide wire 1072, indicated by the double arrow 1318.

Figure 19:
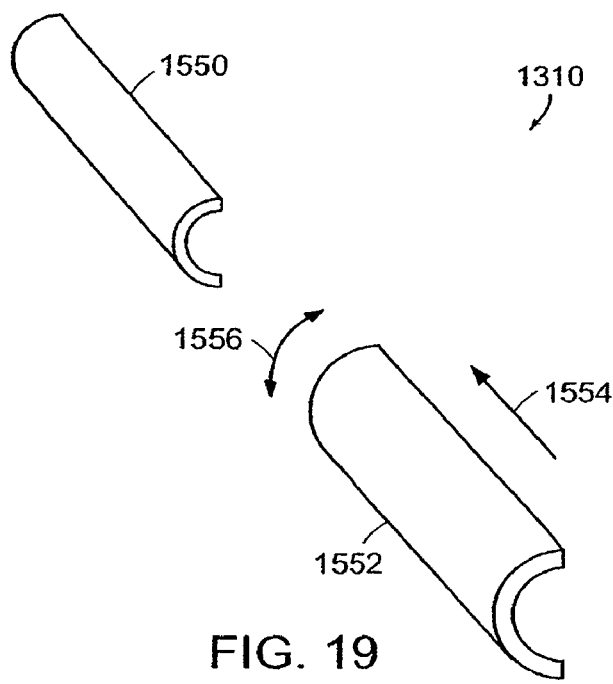
FIGS. 19, 19A and 19B illustrate yet another embodiment of the connector.
Figure 19A:
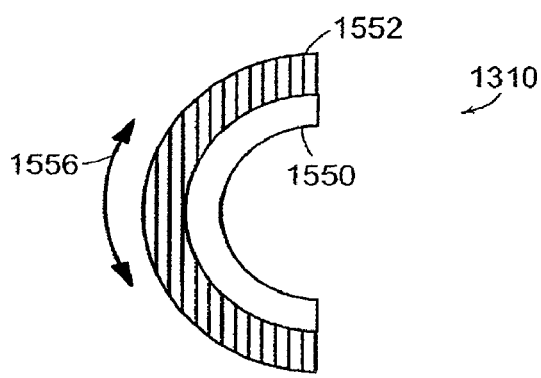
Figure 19B:
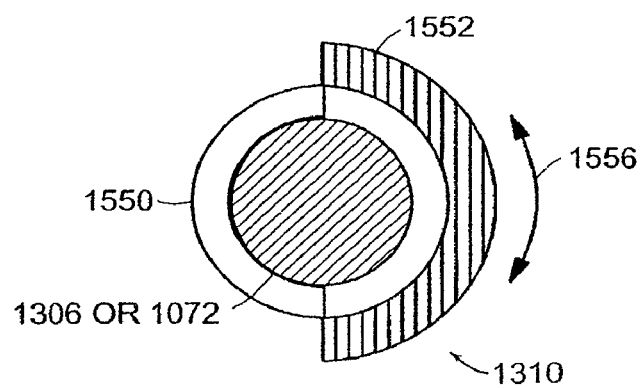

Referring now to FIGS. 19, 19A and 19B, there is shown another embodiment of the connector 1310. In this embodiment, the connector 1310 includes an inner 1550 and an outer 1552 C-shaped rings. To grasp the leg 1306 or guide wire 1072, the outer ring 1552 is slid over the inner ring 1550 in the direction 1554. The guide wire 1072 or the leg 1306 of the catheter 1070 is placed in the inner ring 1550, and the outer ring 1552 is then rotated or twisted in the direction 1556 around the inner ring 1550, thereby capturing the leg 1306 or guide wire 1072. Alternatively, the leg 1306 or guide wire 1072 can first be placed in the inner 1550 and outer 1554 rings, and then the outer ring 1554 can be rotated about the leg or catheter and subsequently slid over the inner ring 1550.

Yet another embodiment of the connector 1310 is shown in FIGS. 20A and 20B. In this embodiment, the connector 1310 includes a pin vise 1600 provided with slot 1602 cut along its length, and a sleeve 1604 that is threaded onto the pin vise 1600. The pin vise is operated by turning the sleeve 1604 so that as it threads onto the vise 1600 in the direction 1606 which causes the slot 1602 to narrow. Thus to secure the leg 1306 or guide wire 1072 to the drive mechanism 1308, the leg or guide wire is first placed into the slot 1602 as shown in FIG. 20B. The operator then rotates the sleeve 1604 to thread it over the pin vise 1600, and hence to close the slot 1602 about the leg or guide wire until the pin vise is sufficiently tightened about the leg 1306 or guide wire 1072.

This invention can be implemented and combined with other applications, systems, and apparatuses, for example, those discussed in greater detail in U.S. Provisional application No. 60/332,287, filed Nov. 21, 2001, the entire contents of which are incorporated herein by reference, as well as those discussed in greater detail in each of the following documents, all of which are incorporated herein by reference in theft entirety:

U.S. application Ser. No. 09/783,637 filed Feb. 14, 2001, which is a continuation of PCT application Ser. No. PCT/US00/12553 filed May 9, 2000, which claims the benefit of U.S. Provisional application Ser. No. 60/133,407 filed May 10, 1999; U.S. application entitled "Articulated Apparatus for Telemanipulator System," by Brock and Lee, U.S. application Ser. No. 10/208,807, filed Jul. 29, 2002, which is a continuation of U.S. application Ser. No. 09/827,503 filed Apr. 6, 2001, now U.S. Pat. No. 6,432,112 issued Aug. 13, 2002, which is a continuation of U.S. application Ser. No. 09/746,853 filed Dec. 21, 2000, now U.S. Pat. No. 6,692,485 issued Feb. 17, 2004, which is a divisional of U.S. application Ser. No. 09/375,666 filed Aug. 17, 1999, now U.S. Pat. No.

6,197,017 issued on Mar. 6, 2001, which is a continuation of U.S. application Ser. No. 09/028,550 filed Feb. 24, 1998, now abandoned; PCT application Serial No. PCT/US01/11376 filed Apr. 6, 2001, which claims priority to U.S. application Ser. No. 09/746,853 filed Dec. 21, 2000, and U.S. application Ser. No. 09/827,503 filed Apr. 6, 2001; U.S. application Ser. Nos. 10/014,143, 10/012,845, 10/008,964, 10/013,046, 10/011,450, 10/008,457, and Ser. No. 10/008,871, all filed Nov. 16, 2001 and all of which claim benefit to U.S. Provisional Application No. 60/279,087 filed Mar. 27, 2001; U.S. application Ser. No. 10/077,233 filed Feb. 15, 2002, which claims the benefit of U.S. Provisional Application No. 60/269,203 filed Feb. 15, 2001; U.S. application Ser. No. 10/097,923 filed Mar. 15, 2002, which claims the benefit of U.S. Provisional Application No. 60/276,151 filed Mar. 15, 2001; U.S. application Ser. No. 10/034,871 filed Dec. 21, 2001, which claims the benefit of U.S. Provisional Application No. 60/257,816 filed Dec. 21, 2000; U.S. application Ser. No. 09/827,643 filed Apr. 6, 2001, which claims the benefit of U.S. Provisional application No. 60/257,869 filed Dec. 21, 2000, and U.S. Provisional Application No. 60/195,264 filed Apr. 7, 2000.

While this invention has been particularly shown and described with references to preferred embodiments thereof, it will be understood by those skilled in the art that various changes in form and details may be made therein without departing from the scope of the invention encompassed by the appended claims.

For example, although a detector for sensing relative movement between adjacent catheters has been described, a detector for sensing movement of any one or more of the catheters relative to a base position that may or may not be a location on a particular one of the catheters can be employed. Also described herein is the use of cabling through the catheters for controlling the movement of the catheters. In certain embodiments a piezo-electric arrangement may be employed in which electrical signal wires would extend through the catheter system for actuation of a mechanical (piezoelectric) member to provide motion of the distal end of the catheter.

What is claimed is:

1. A medical system for performing a surgical procedure on a patient, comprising:
   a first medical probe having indicia, the first medical probe being configured for insertion into a lumen or vessel of the patient;
   a second medical probe in a coaxial arrangement with the first medical probe, the second medical probe being configured for insertion into the lumen or vessel;
   a detector fixedly coupled to the second medical probe and configured for insertion into and advancement through the lumen or vessel along with the second medical probe, wherein the detector detects passage of the indicia as the first and second medical probes are moved relative to each other within the lumen or body vessel;
   an electromechanical driver coupled to the first and second medical probes, the electromechanical driver being operable to move the first and second medical probes; and
   a controller configured for directing the electromechanical driver to move the first and second medical probes relative to each other within the lumen or body vessel based on signals received from the detector when the detector is positioned within the lumen or body vessel.

2. The medical system of claim 1, further comprising a user interface configured for receiving at least one command, wherein the controller is configured for directing the electromechanical driver in response to the at least one command.

3. The medical system of claim 1, wherein the controller is coupled to the electromechanical driver via external cabling.

4. The medical system of claim 1, wherein the first medical probe is an inner medical probe, and the second medical probe is an outer medical probe.

5. The medical system of claim 1, wherein the detector is an optical detector.

6. The medical system of claim 1, wherein the controller is configured for directing the electromechanical driver to linearly translate the first and second medical probes relative to each other, the indicia is disposed along a length of the first medical probe, the detector is configured for detecting a linear passage of the indicia as the first and second medical probes are linearly translated relative to each other, and the controller is configured for receiving signals from the detector indicating the relative linear translation between the first and second medical probes.

7. The medical system of claim 1, wherein the controller is configured for directing the electromechanical driver to axially rotate the first and second medical probes relative to each other, the indicia is disposed along a circumference of the first medical probe, the detector is configured for detecting a rotational passage of the indicia as the first and second medical probes are axially rotated relative to each other, and the controller is configured for receiving signals from the detector indicating the relative axial rotation between the first and second medical probes.

8. The medical system of claim 1, wherein the first and second medical probes are flexible catheters.

9. The medical system of claim 1, wherein the first medical probe further includes an articulating tool, and the controller is configured for directing the electromechanical driver to actuate the articulating tool.

10. The medical system of claim 1, wherein the controller is operable to direct the electromechanical driver to move the second medical probe relative to the first medical probe.

11. The medical system of claim 1, wherein the controller is operable to direct the electromechanical driver to move the first medical probe and the second medical probe.

12. A method for monitoring relative positions of a first medical probe and a second medical probe inside of a patient, the second medical probe being in a coaxial arrangement with the first medical probe, the method comprising:
   directing an electromechanical driver coupled to the first medical probe and the second medical probe to move the first medical probe and the second medical probe relative to each other, the first medical probe and the second medical probe being inserted into a lumen or vessel in the patient, the first medical probe having indicia, the second medical probe having a detector for sensing a passage of the indicia as the first medical probe and the second medical probe are moved relative to each other, wherein the detector is inserted into the lumen or vessel, and wherein a position of the detector changes with movement of the second medical probe as the second medical probe is repositioned within the lumen or vessel; and
   detecting signals indicating the relative movement between the first medical probe and the second medical probe.

13. The method of claim 12, wherein the first medical probe is an inner medical probe and the second medical probe is an outer medical probe.

14. The method of claim 12, wherein the detector is an optical detector.

15. The method of claim 12, wherein the first medical probe and the second medical probe are linearly translated relative to each other, and the relative linear movement between the first medical probe and the second medical probe is detected.

16. The method of claim 12, wherein the first medical probe and the second medical probe are rotationally translated relative to each other, and the relative rotational movement between the first medical probe and the second medical probe is detected.

17. The method of claim 12, wherein an articulating tool is attached to the first medical probe, the method further comprising directing the electromechanical driver to actuate the articulating tool.

18. The method of claim 12, wherein the second medical probe is moved relative to the first medical probe.

19. The method of claim 12, wherein the first medical probe and the second medical probe are independently moved relative to each other.

20. A method for monitoring relative positions of a first medical probe and a second medical probe inside of a patient, the second medical probe being in a coaxial arrangement with the first medical probe, the method comprising:

directing an electromechanical driver coupled to the first medical probe and the second medical probe to controllably bend the first medical probe and the second medical probe and to move the first medical probe and the second medical probe relative to each other, the first medical probe and the second medical probe being inserted into the patient, the first medical probe having indicia, the second medical probe having a detector for sensing a passage of the indicia as the first medical probe and the second medical probe are moved relative to each other, wherein the detector is inserted into the patient, and wherein a position of the detector changes with movement of the second medical probe and as the second medical probe is repositioned within the patient; and detecting signals indicating the relative movement between the first medical probe and the second medical probe.

\* \* \* \* \*